(12) United States Patent
Tyrrell et al.

(10) Patent No.: US 6,787,648 B2
(45) Date of Patent: Sep. 7, 2004

(54) COMPOSITIONS AND METHODS FOR DETECTING RAPHIDOPHYTES

(75) Inventors: John V. Tyrrell, Monterey, CA (US);
Patricia R. Bergquist, Auckland (NZ);
Peter L. Bergquist, Auckland (NZ);
Christopher A. Scholin, Capitola, CA (US)

(73) Assignee: Monterey Bay Aquarium Research Institute, Moss Landing, CA (US)

( * ) Notice: Subject to any disclaimer, the term of this patent is extended or adjusted under 35 U.S.C. 154(b) by 492 days.

(21) Appl. No.: 09/780,113

(22) Filed: Feb. 9, 2001

(65) Prior Publication Data

US 2004/0023212 A1 Feb. 5, 2004

Related U.S. Application Data

(63) Continuation-in-part of application No. 09/596,136, filed on Jun. 16, 2000, now abandoned.
(60) Provisional application No. 60/141,362, filed on Jun. 28, 1999.

(51) Int. Cl.[7] .................. C07H 21/02; C07H 21/04; C12Q 1/68; C12P 19/34
(52) U.S. Cl. .................. 536/24.32; 536/23.1; 536/24.3; 536/24.33; 435/6; 435/91.2
(58) Field of Search ................ 435/6, 91.2, 91.5, 435/91.51; 536/23.1, 24.3, 24.32, 24.33

(56) References Cited

FOREIGN PATENT DOCUMENTS

WO  WO 97/44489  11/1997

OTHER PUBLICATIONS

Asai (Nippon Kagakkai Koen Yokoshu, 1998, vol. 75, p. 315).*
Lee. GenBank Accession No. AF042820, Feb. 1, 1998.*
van den Hoek et al., "Heterokontophyta: Class Raphidophyceae" ALGAE An Introduction to Phycology, pp. 160–163.
Ahmed, M. S., "Properties of hemagglutinins newly separated from toxic phytoplankton", Biohimica et Biophisica Acta 1243:509–512 (1995).
Amann R. I., "Fluorescently labeled, rRNA–targeted oligonucleotide probes in the study of microbial ecology", Molecular Ecology 4: 543–554 (1995).
Amann et al., "Phylogenetic identification and in situ detection of individual microbial cells without cultivation", Microbiol. Rev. 59: (1) 143–169 (1995).
Black et al., "The effects of Heterosigma akashiwo on juvenile Oncorhynchus tshawytscha and its implications for fish culture", J. Appl. Ichthyol. 7: 168–175 (1991).

(List continued on next page.)

Primary Examiner—Carla Myers
(74) Attorney, Agent, or Firm—Morrison & Foerster LLP

(57) ABSTRACT

Effective management of finfish stocks to avoid or mitigate the threat of fish-killing phytoplankton is of increasing concern, particularly in temperate seas. Intensive spatial and temporal sampling is required to monitor and quantify potentially harmful species, so that prior warning can be received of an imminent bloom. The use of large-subunit rRNA (LSU rRNA)-targeted oligonucleotide probes based on the sandwich hybridization assay to detect the fragile species *Heterosigma akashiwo* (Hada) Hada and *Fibrocapsa japonica* Toriumi & Takano (Raphidophyceae) is disclosed. Species-specific sandwich hybridization assays were successfully developed for various Raphidophytes.

3 Claims, 3 Drawing Sheets

A

B

OTHER PUBLICATIONS

Chang et al., "First record of a Heterosigma (Raphidophyceae) bloom with associated mortality of cage-reared salmon in Big Glory Bay", New Zealand, NZ. J. Mar. Freshwater. Res. 24: 461–469 (1990).

DeLong et al., "phylogenetic stains: ribosomal RNA–based probes for the identification of single cells", Science 243: 1360–1363 (1989).

Embley et al., "The use of rRNA sequences and fluorescent probes to investigate the phylogenetic positions of the anaerobic ciliate *Metopus palaeformis* and its archaeobacterial endosymbiont", J. Gen. Microbiol. 138: 1479–1487 (1992).

Endo et al., "Neurotoxin–induced cardiac disorder and its role in the death of fish exposed to *Chattonella marina*", Mar. Biol. 112: 371–376 (1992).

Field et al., "Molecular phylogeny of the animal kingdom", Science 239: 748–753 (1988).

Giovanoni et al., "Phylogenetic group–specific oligodeoxynucleotide probes for identification of single microbial cells", J. of Bacteriology 170: 720–726 (1988).

Khan et al., "Neurotoxins in a toxic red tide of Heterosigma akashiwo (Raphidophyceae) in Kagoshima Bay, Japan", Aquaculture and Research 28(1): 9–14 (1997).

Khan et al., "Growth characteristics of a neurotoxin–producing chloromonad *Fibrocapsa japonica* (Raphidophyceae)", J. of the World Aquaculture Society 27(3): 247–253 (1996).

Khan et al., "Properties of neurotoxins separated from a harmful red tide organism *Chattonella marina*", The Israeli J. of Aquaculture–Bamidgeh, 47(3–4: 137–141 (1995).

Khan et al., "Effects of physiological factors on morphology and motility of Chattonella Antigua (Raphidophyceae)", Botanica Marina 38: 347–353 (1995).

MacKenzie L., "Toxic and noxious phytoplankton in Big Glory Bay, Stewart Island, New Zealand", J. of App. Phycol. 3: 19–34 (1991).

Mille P. E. et al., "Identification and enumeation of cultured and wild Pseudo–nitzschia (Bacillariophyceae) using species–specific LSU rRNA—targeted fluorescent probes and filterbased whole cell hybridization", J. Phycol. 34: 371–382 (1998).

Miller P. E. et al., "Identification of cultured Pseudo–nitzschia (Bacillariophyceae) using species–specific LSU rRNA–targeted fluorescent probes", J. of Phycol. 32: 646–655 (1996).

Onoue Y., et al., "Separation of toxins from harmful red tides occurring along the coast of Kagoshima prefecture", In: Red Tides: Biology, Environmental Science and Toxicology (Ed. by T. Okaichi, D. M. Anderson & T Nemoto), pp. 371–374, Elsevier Science Press, N. Y. (1989).

Scholin, C. A. et al., "Detection and quantification of Pseudo–nitzschia australis in cultured and natural populations using LSU rRNA–targeted probes", Limnol. Oceanogr. 42: 1265–1272 (1998).

Scholin, C. A., "Identification of Pseudo–nitzschia autralis (Bacillariophyceae) using rRNA targeted probes in whole cell and sandwich hybridisation formats", Phycologia 35 (3): 190–197 (1996).

Tomas, "*Olisthodiscus luteus* (Chyrsophyceae) I. Effects of salinity and temperature on growth, motility and survival", J. Phycol. 14: 309–313 (1978).

Tyrrell et al., "Phylogeny of the Raphidophytes *Heterosigma carterae* and *Chattonella antiqua* using 'V4' domain SSU rDNA sequences", Biochem. Syst. Ecol. 24: (3) 221–235 (1978).

Watanabe et al., " Effects of physico–chemical factors and nutrients on the growth of Heterosigma akashiwo Hada from Osaka Bay, Japan", Jap. J. Phycol. 30: 279–288 (1982).

Yamochi S., "Mechanisms for outbreak of Heterosigma akashiwo red tide in Osaka Bay, Japan: part 1, Nutrient factors involved in controlling the growth of Heterosigma akashiwo Hada", J. Oceanogr. Soc. Japan 39: 310–316 (1983).

Yamochi et al., "Mechanisms to initiate a Heterosigma akashiwo red tide in Osaka Bay, II. Diel vertical migration", Mar. Biol. 23: 255–261 (1984).

* cited by examiner

SEQUENCE LISTING

```
<160> NUMBER OF SEQ ID NOS: 30

<210> SEQ ID NO 1
<211> LENGTH: 18
<212> TYPE: DNA
<213> ORGANISM: Artificial Sequence
<220> FEATURE:
<223> OTHER INFORMATION: Artificial oligonucleotide probe

<400> SEQUENCE: 1
gwattaccgc ggckgctg                                                 18

<210> SEQ ID NO 2
<211> LENGTH: 18
<212> TYPE: DNA
<213> ORGANISM: Artificial Sequence
<220> FEATURE:
```

-continued

<223> OTHER INFORMATION: Artificial oligonucleotide probe

<400> SEQUENCE: 2
cagcmgccgc ggtaatwc                      18

<210> SEQ ID NO 3
<211> LENGTH: 19
<212> TYPE: DNA
<213> ORGANISM: Artificial Sequence
<220> FEATURE:
<223> OTHER INFORMATION: Artificial oligonucleotide probe

<400> SEQUENCE: 3
cgactgagca cgcaccttt                     19

<210> SEQ ID NO 4
<211> LENGTH: 21
<212> TYPE: DNA
<213> ORGANISM: Artificial Sequence
<220> FEATURE:
<223> OTHER INFORMATION: Artificial oligonucleotide probe

<400> SEQUENCE: 4
gcgacggcaa aaagaccagg a                  21

<210> SEQ ID NO 5
<211> LENGTH: 19
<212> TYPE: DNA
<213> ORGANISM: Artificial Sequence
<220> FEATURE:
<223> OTHER INFORMATION: Artificial oligonucleotide probe

<400> SEQUENCE: 5
gcatgttgaa acgctccag                     19

<210> SEQ ID NO 6
<211> LENGTH: 20
<212> TYPE: DNA
<213> ORGANISM: Artificial Sequence
<220> FEATURE:
<223> OTHER INFORMATION: Artificial oligonucleotide probe

<400> SEQUENCE: 6
agcaaaggtc ctccgtccta                    20

<210> SEQ ID NO 7
<211> LENGTH: 27
<212> TYPE: DNA
<213> ORGANISM: Artificial Sequence
<220> FEATURE:
<223> OTHER INFORMATION: Artificial oligonucleotide probe

<400> SEQUENCE: 7
tactctcttt tcaaaagtct tttcatc            27

<210> SEQ ID NO 8
<211> LENGTH: 22
<212> TYPE: DNA
<213> ORGANISM: Artificial Sequence
<220> FEATURE:
<223> OTHER INFORMATION: Artificial oligonucleotide probe

<400> SEQUENCE: 8
ccgcttcact cgccgttact ag                 22

```
<210> SEQ ID NO 9
<211> LENGTH: 25
<212> TYPE: DNA
<213> ORGANISM: Artificial Sequence
<220> FEATURE:
<223> OTHER INFORMATION: Artificial oligonucleotide probe

<400> SEQUENCE: 9
tcatctttcc ctcacggtac ttgtt                                    25

<210> SEQ ID NO 10
<211> LENGTH: 19
<212> TYPE: DNA
<213> ORGANISM: Artificial Sequence
<220> FEATURE:
<223> OTHER INFORMATION: Artificial oligonucleotide probe

<400> SEQUENCE: 10
cggctggaca cgcttctgt                                           19

<210> SEQ ID NO 11
<211> LENGTH: 21
<212> TYPE: DNA
<213> ORGANISM: Artificial Sequence
<220> FEATURE:
<223> OTHER INFORMATION: Artificial oligonucleotide probe

<400> SEQUENCE: 11
cagcacgaaa tatgaccccc g                                        21

<210> SEQ ID NO 12
<211> LENGTH: 23
<212> TYPE: DNA
<213> ORGANISM: Artificial Sequence
<220> FEATURE:
<223> OTHER INFORMATION: Artificial oligonucleotide probe

<400> SEQUENCE: 12
ccatgggaca cagcgcgcac tac                                      23

<210> SEQ ID NO 13
<211> LENGTH: 22
<212> TYPE: DNA
<213> ORGANISM: Artificial Sequence
<220> FEATURE:
<223> OTHER INFORMATION: Artificial oligonucleotide probe

<400> SEQUENCE: 13
tacaaaccaa ggtgcactaa tg                                       22

<210> SEQ ID NO 14
<211> LENGTH: 27
<212> TYPE: DNA
<213> ORGANISM: Artificial Sequence
<220> FEATURE:
<223> OTHER INFORMATION: Artificial oligonucleotide probe

<400> SEQUENCE: 14
aactctcttt ccaaagttct tttcatc                                  27

<210> SEQ ID NO 15
<211> LENGTH: 23
<212> TYPE: DNA
<213> ORGANISM: Artificial Sequence
<220> FEATURE:
<223> OTHER INFORMATION: Artificial oligonucleotide probe
```

-continued

```
<400> SEQUENCE: 15
accacgactg agcacgcacc ttt                                              23

<210> SEQ ID NO 16
<211> LENGTH: 20
<212> TYPE: DNA
<213> ORGANISM: Artificial Sequence
<220> FEATURE:
<223> OTHER INFORMATION: Artificial oligonucleotide probe

<400> SEQUENCE: 16
agcccgggac cacgactgag                                                  20

<210> SEQ ID NO 17
<211> LENGTH: 23
<212> TYPE: DNA
<213> ORGANISM: Artificial Sequence
<220> FEATURE:
<223> OTHER INFORMATION: Artificial oligonucleotide probe

<400> SEQUENCE: 17
gagcaaaggt cctccgtcct aac                                              23

<210> SEQ ID NO 18
<211> LENGTH: 27
<212> TYPE: DNA
<213> ORGANISM: Artificial Sequence
<220> FEATURE:
<223> OTHER INFORMATION: Artificial oligonucleotide probe

<400> SEQUENCE: 18
tactctcttt tcaaaagtct tttcatc                                          27

<210> SEQ ID NO 19
<211> LENGTH: 22
<212> TYPE: DNA
<213> ORGANISM: Artificial Sequence
<220> FEATURE:
<223> OTHER INFORMATION: Artificial oligonucleotide probe

<400> SEQUENCE: 19
ccgcttcact cgccgttact ag                                               22

<210> SEQ ID NO 20
<211> LENGTH: 25
<212> TYPE: DNA
<213> ORGANISM: Artificial Sequence
<220> FEATURE:
<223> OTHER INFORMATION: Artificial oligonucleotide probe

<400> SEQUENCE: 20
tcatctttcc ctcacggtac ttgtt                                            25

<210> SEQ ID NO 21
<211> LENGTH: 21
<212> TYPE: DNA
<213> ORGANISM: Artificial Sequence
<220> FEATURE:
<223> OTHER INFORMATION: Artificial oligonucleotide probe

<400> SEQUENCE: 21
cggctggaca cgcttctgta g                                                21

<210> SEQ ID NO 22
<211> LENGTH: 27
```

```
<212> TYPE: DNA
<213> ORGANISM: Artificial Sequence
<220> FEATURE:
<223> OTHER INFORMATION: Artificial oligonucleotide probe

<400> SEQUENCE: 22
aactctcttt ccaaagttct tttcatc                                              27

<210> SEQ ID NO 23
<211> LENGTH: 23
<212> TYPE: DNA
<213> ORGANISM: Artificial Sequence
<220> FEATURE:
<223> OTHER INFORMATION: Artificial oligonucleotide probe

<400> SEQUENCE: 23
agagtagctg agcacgcatc tct                                                  23

<210> SEQ ID NO 24
<211> LENGTH: 687
<212> TYPE: DNA
<213> ORGANISM: Chattonella antiqua

<400> SEQUENCE: 24
ttcttgaagc ggaggaaaag aaccaactcg gattccctag taacggcgag tgaagcggga          60
agagctcatg ttgtaaatct ggatgaggat tcctcgtccc gaattgtagt ctagagatgc         120
gtgctcagct actctccagg gctaagtctg tttgtgaaag acagcatcat ggacggtgat         180
aatccggttc ttgccttgga tgttgtagcg tcttgagccg tcctcaacga gtcgagttgc         240
ttgggattgc agctctaagc gggtggtaaa ttccatctaa agctaaatat tggtgggaga         300
ccgatagcga acaagtaccg tgagggaaag atgaaaagac ctttgaaaag agagttaaat         360
agtacctgaa actgctgaaa gggaagcgaa tgaagtcagt gttgctcttt gttctctgca         420 tcctcccctgc ggggattgtg tatcgaggac tttgagcttg tcaggatgag ttctctgccg        480
cgggatatgg tttgtgagct ggatgcttct gctgaactca ctctctctgt cgtggcttgg         540
actgaggttc catcttgccg ttgcctgctt gttactctcc tgttgctgtt tctgtcctac         600
tgcttgcagt gttcggttgc agtgattgga ctgtgcaagt tatgcatgca aggtcaggat         660
cctgacgaat ggctttatta acccgaa                                             687

<210> SEQ ID NO 25
<211> LENGTH: 681
<212> TYPE: DNA
<213> ORGANISM: Chattonella subsalsa

<400> SEQUENCE: 25
gcggaggaaa agaaccaact cggattccct agtaacggcg agtgaagcgg gaagagctca         60
tgttgtaaat ctggatgagg gttcctcgtc ccgaattgta gtctagagat gcgtgctcag        120
ctactctcca gggctaagtc tgtttgtgaa agacagtgtc atggacggtg ataacccggt        180
tcttgccttg gatgttgtag cgttttgagc cgtcctcaac gagtcgagtt gcttgggatt        240
gcagctctaa gtgggtggta aattccatct aaagctaaat attggtggga gaccgatagc        300
gaacaagtac cgtgagggaa agatgaaaag aactttgaaa agagagttaa atagtacctg        360
aaactgctga agggaagcg aatgaagtca gtgttgctct ttgtgctctg catcctccct         420
gcggggattg tgtatcgagg actttgagct tgtcaggatg agttctctgc cgcgggatat        480
gttttgtatg ctggatgctt tttgcggaac atacattctc tgtcgtggct tggactgagg        540
```

```
ttccatcttg ccgttgcctg tgcgttcctc tcccgttgct gtctctgttc tactgcttgc      600
agtgctcagt tgcagtagtt ggactgtgcg tattatgcat gcaaggtcag gatcctgacg      660
aatggcttta ttcacccgca a                                                681
```

<210> SEQ ID NO 26
<211> LENGTH: 703
<212> TYPE: DNA
<213> ORGANISM: Fibrocapsa japonica

<400> SEQUENCE: 26

```
cagaggaaaa gaaacaactc ggattcccta gtaacggcga gtgaagcggg aacagctcat       60
gatgtaaatc tgggtgacgt ttcgttaccc cgaattgtag tctacagaag cgtgtccagc      120
cgcgccccct ggcaaagtcc cctggaacgg ggcatcgtgg acggtgacaa tccggttcat      180
gcctggggtg tcgcgtgtgt acgggccgtt tcaacgagt cgagttgctt gggattgcag       240
ctctaagcgg gtggtaaatt ccatctaaag ctaaatattg gtgggagacc gatagcgaac      300
aagtaccgtg agggaaagat gaaaagaact tggaaagag agttaaacag tacctgaaat       360
tgctgaaagg gaagcgaagg aagtcagtgt atgccggggg tcatatttcg tgctgccttg      420
aggggtagtg cgcgctgtgt cccatgggct ggtcaggatg ggtttgttcc gcggagatt       480 cccagggttg aggtaggtcc ttttggattg tcagcaaccc tgtggcatgt cgtggttcgg      540
accgaggcat tagtgcacct tggtttgtac ggtttttatat gcgtgatcat gtctgtgaca    600
gcatgctgtg gcggttgtgt tatcgtttat ttgccttgca ttccccgtgc gctctagatc      660
ctgtcaaatg gctttcttcc acctcttgaa agacggacca agg                        703
```

<210> SEQ ID NO 27
<211> LENGTH: 715
<212> TYPE: DNA
<213> ORGANISM: Heterosigma akashiwo

<400> SEQUENCE: 27

```
acccgctgaa tttaagcata taattaaggg gaggaaaaga aaccaactcg gattccccta      60
gtaacggcga gtgaagcggg aagagctcat gttgtaaatc tccagcttgc tggcgaattg     120
tagtctaaag gtgcgtgctc agtcgtggtc ccgggctaag tctgttggaa acagcatca     180 tggacggtga caatccggtt cttgcctggg gtcccgcggc gtacgagccg tttccgacga     240
gtcgtgttgc ttgggattgc agcactaagt gggtggtaaa ttccatctaa agctaaatat    300
tggtgggaga ccgatagcga acaagtaccg tgagggaaag atgaaaagac ttttgaaaag    360
agagtaaaat agtacctgaa actgctgaaa gggaagcgat tgaagtcagt gttgctcctg    420 gtcttttttgc cgtcgccccc gtgggggttg cggcgtgggg cctggagcgt tcaacatgc    480 gttctgttcc gcgggaaatg ttcagtgtgc tggaacttcg gggaaacgca ctgttcttgt    540
cgtggttagg acggaggacc tttgctcctt tgactgcgcg ttcctctctc gggtatgctg     600
gtgtctactg cttgcagttt tcatttttcat gcttgcgact gtgcgtgtta ttcatgagcg    660
aacatgatgt tgaagaaatg gctttaatta ccccgtcttg aaacacggac caagg           715
```

<210> SEQ ID NO 28
<211> LENGTH: 681
<212> TYPE: DNA
<213> ORGANISM: Vacuolaria virescens

<400> SEQUENCE: 28

-continued

```
aacggaggaa aagaatccaa ctcggattcc ctagtaacgg cgagtgaagc gggaagagct      60
caagttgaaa atctgggtgg ggcctcccca tcccgaattg tagtctagag acgcgtgctc     120
agccgtgctc cagggctaag tctgttggaa aacagcatca tggacggtga taatccggtt     180
cttgccctgg gtgttgcggt gtacgagccg tgatccacga gtcgagttgc ttgggattgc     240
agctctaagc gggtggtaaa ttccatctaa agctaaatat tggtgggaga ccgatagcaa     300
acaagtaccg tgagggaaag atgaaaagaa ctttgaaaag agagttaaaa agtacctgaa     360
attgctgaaa gggaagcgaa tgaagtcagt gtctgctcct ggttgtattt tcggagtccc     420 tgcgggatt ccggcactgt ggcctggagc atgtcaggat gagttctctg ccgtgggata      480
tgtttggtgg gattggtacc ttcggggaaa cccgccactc ttgtcatggc ttggactgag     540
gttccatctc gccgtttgcc tgcccgtcgc tctctgccgg ttgttgctgt cctactgctt     600
gcagtgctca gctgcagctg actgactgtg cgggtcatgc atgcgaggtc aggatcctga     660
ggactggccg taataaccca a                                                681
```

<210> SEQ ID NO 29
<211> LENGTH: 20
<212> TYPE: DNA
<213> ORGANISM: Artificial Sequence
<220> FEATURE:
<223> OTHER INFORMATION: Artificial PCR Primer

<400> SEQUENCE: 29
acccgctgaa tttaagcata                    20

<210> SEQ ID NO 30
<211> LENGTH: 20
<212> TYPE: DNA
<213> ORGANISM: Artificial Sequence
<220> FEATURE:
<223> OTHER INFORMATION: Artificial PCR Primer

<400> SEQUENCE: 30
ccttggtccg tgtttcaaga                    20

COMPOSITIONS AND METHODS FOR DETECTING RAPHIDOPHYTES

RELATED APPLICATION

This application is a Continuation in Part Application of application Ser. No. 09/596,136 filed Jun. 16, 2000, now abandoned, which claims' priority under 35 U.S.C. §119(e) of U.S. provisional patent application No. 60/141,362 filed Jun. 28, 1999, each of which are hereby incorporated by reference in its entirety.

FIELD OF THE INVENTION

The present invention relates, in general, to compositions, methods and diagnostic kits useful for the detection of fish-killing raphidophyte algae using rRNA-targeted probes.

BACKGROUND OF THE INVENTION

Raphidophytes are algae of the class Raphidophyceae. Raphidophytes such as *Heterosigma akashiwo* (Hada) ex Sournia and *Fibrocapsa japonica* Toriumi & Takano are well known in temperate seas as causative agents for mass finfish kills in seapen aquaculture. For example, during the summer of 1989, a large bloom of *Heterosigma akashiwo* in Big Glory Bay, Stewart Island, New Zealand, caused extensive mortality of caged Quinnat salmon (*Onchorynchus tshawytscha*), the loss being valued at NZD $4.5 million [Chang F. H., Anderson, C. & Boustead, N. C. 1990. This event was the first record of a Heterosigma (Rapbidophyceae) bloom with associated mortality of cage-reared salmon in Big Glory Bay, New Zealand. *NZ J. Mar. Freshwater. Res.* 24: 461–469; MacKenzie L. 1991.

Harmful algal bloom research and monitoring has traditionally been based on ecological and microbiological measurements which are laborious, time-consuming, and reliant on experienced operators. The rapid identification and enumeration of harmful raphidophyte species is crucial for the management of cultured finfish, shellfish and wild resources in order to avoid stock loss.

Thus, there is a need to develop a test system for rapid, sensitive and cost effective analysis of Raphidophytes that permits as near as possible real time monitoring of the algae.

SUMMARY OF THE INVENTION

In order to meet these needs, the present invention is directed to compositions, methods and diagnostic kits useful for the detection of fish-killing raphidophyte algae using rRNA targeted probes. The probes comprise a segment of nucleic acid capable of selectively hybridizing, under selective hybridizing conditions, to large-subunit ribosomal RNA from raphidophytes.

The probes include those oligonucleotide probes having sequences selected from SEQ ID NO: 3 through SEQ ID NO: 23 and homologous sequences. The probes maybe utilized in various combinations including pairwise. The probes of the invention may be of the formula $[X-Y-Z]_n$ where X is a sequence of 0 to 100 nucleotides or nucleotide analogs that are non-homologous to conserved or nonconserved regions of raphidophyte nucleic acid. In the formula, Y is a sequence of 10 to 100 nucleotides or nucleotide analogs that are capable of hybridizing under hybridizing conditions to hypervariable regions of the ribosomal RNA of raphidophytes. Such sequences for Y include those sequences selected from SEQ ID NO:3 through SEQ ID NO:23 and homologous sequences. Furthermore, Z is a sequence of 0 to 100 nucleotides or nucleotide analogs that are non homologous to conserved or non conserved regions of raphidophyte nucleic acid. The sequence of Z may be the same or different from X. Finally, n is 1 to 500 or more.

In addition to compositions, methods are disclosed for the detection of raphidophytes from a marine sample using fluorescent in situ hybridization (F.I.S.H.) and sandwich hybridization assays (S.H.A.). These methods comprise the steps of: permeabilizing the species of raphidophyte to be assayed to expose the ribosomal RNA; contacting the exposed ribosomal RNA, under hybridizing conditions, with oligonynucleotide probes capable of selectively hybridizing to the hypervariable regions of the ribosomal RNA of at least one species of raphidophyte; and detecting hybridization complexes as an indication of the presence of the raphidophyte cell in the sample.

In addition to compositions and methods, there are disclosed herein diagnostic kits for use in determining the presence of raphidophytes which comprise a synthetic oligonucleotide probe complementary to the aforementioned hypervariable or conserved regions of the ribosomal RNA of a raphidophyte species from a marine sample. The kits may include hybridization buffers.

The present invention has utility in providing an easy, sensitive, and specific test for algae which may kill finfish and invertebrates.

BRIEF DESCRIPTION OF THE DRAWINGS

This invention will be better understood by reference to the drawings, in which.

BRIEF DESCRIPTION OF THE SEQUENCE LISTING

Figure 1:
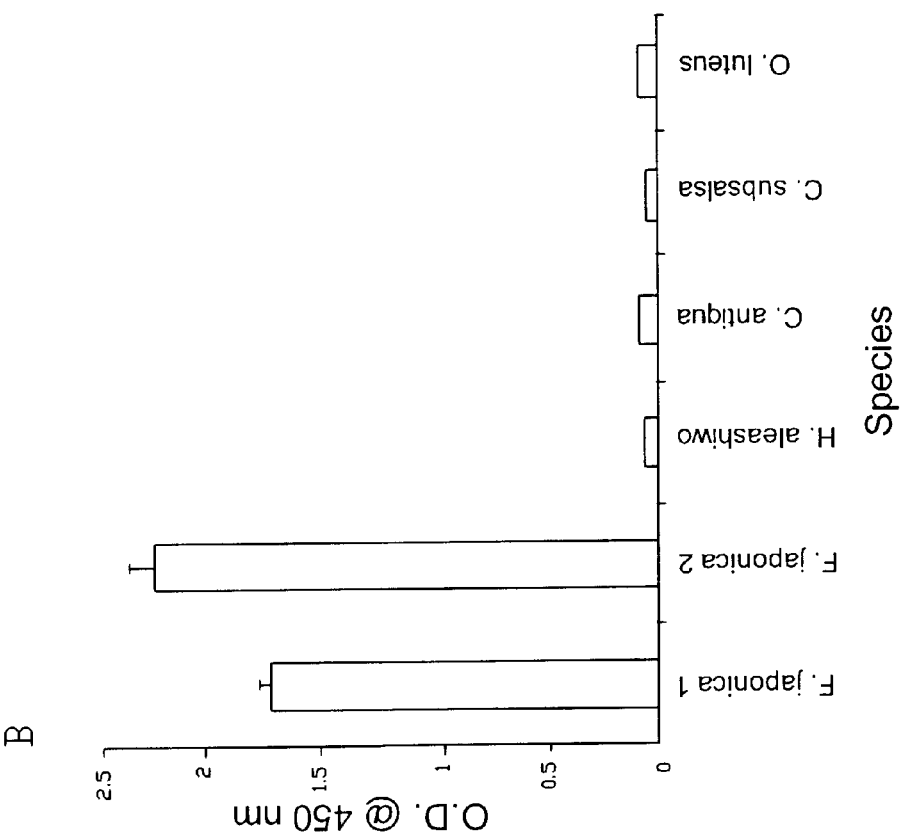
FIG. 1 shows specificity and isolate comparison for the sandwich hybridization assay probe combinations targeted at *H. akashiwo* and *F. japonica*. In A) the probe combination Het1.25aS/Raphid1F, which is targeted at *H. akashiwo*, was screened against a number of *H. akashiwo* isolates and other raphidophyte species. *H. akashiwo* 1 represents the isolate *H. akashiwo* CAWR04; *H. akashiwo* 2=CAWR05; *H. akashiwo* 3=CAWR09 and *H. akashiwo* 4=CAWR14. The *F. japonica* isolate was CAWR02. In B) the probe combination Fib1.25aS/Raphid1F, which is targeted at *F. japonica*, was screened against two *F. japonica* isolates and other raphidophyte species. *F. japonica* 1 represents the isolate CAWR02 and *F. japonica* 2 represents the isolate CAWR03. The *H. akashiwo* isolate was CAWR05.
Figure 1:
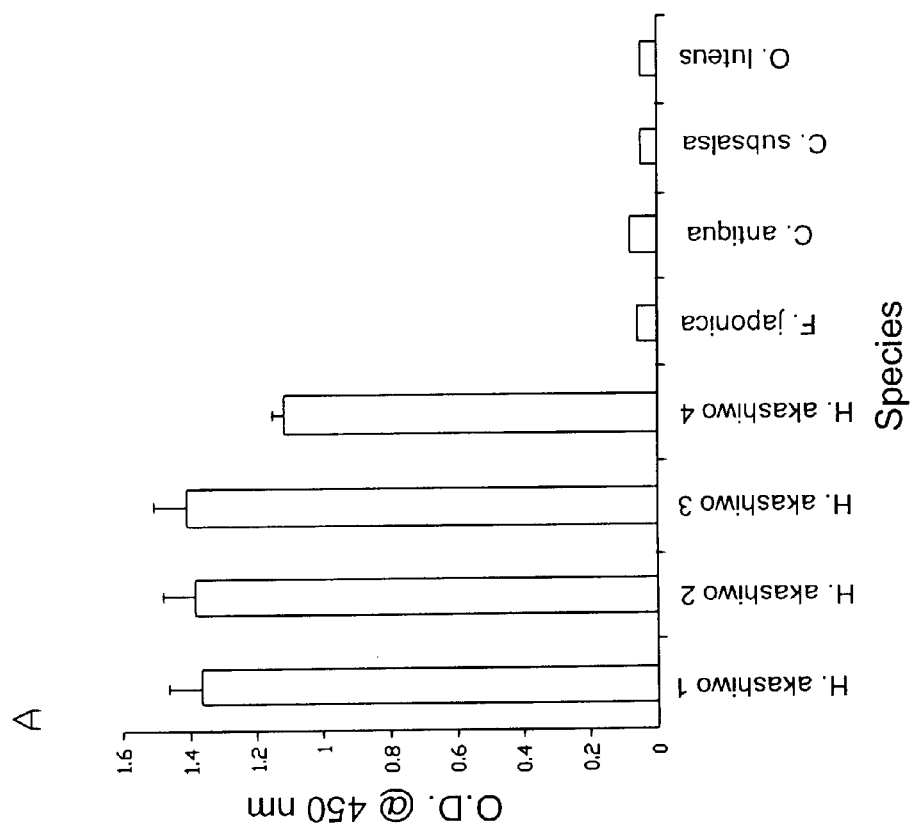

This invention will be better understood by reference to Sequence Listing, in which:

SEQ ID NO: 2 is a Fluorescent In *Situ Hybridization* (F.I.S.H.) positive control probe designated UniC.

SEQ ID NO. 2 is a F.I.S.H. negative control probe designated UniR.

SEQ ID NO: 3 is a F.I.S.H. *H. akashiwo* probe designated Het 1.25F.

SEQ ID NO: 4 is a F.I.S.H. *H. akashiwo* probe designated Het 1.5F.

SEQ ID NO: 5 is a F.I.S.H. *H. akashiwo* probe designated Het 2aF.

SEQ ID NO: 6 is a F.I.S.H. *H. akashiwo* probe designated Het 3F.

SEQ ID NO: 7 is a F.I.S.H. *H. akashiwo* probe designated Het. sig2–3'F.

SEQ ID NO: 8 is a F.I.S.H. Raphidophyceae probe designated Raphid 1F.

SEQ ID NO: 9 is a F.I.S.H. Raphidophyceae probe designated Raphid2F.Raphid 2F.

SEQ ID NO: 10 is a F.I.S.H. *F. japonica* probe designated Fib1.25aF.

SEQ ID NO: 10 is a F.I.S.H. *F. japonica* probe designated Fib 1.5F.

SEQ ID NO: 12 is a F.I.S.H. *F. japonica* probe designated Fib 2F.

SEQ ID NO: 13 is a F.I.S.H. *F. japonica* probe designated Fib 3F.

SEQ ID NO: 14 is a F.I.S.H. *F. japonica* probe designated Fib.sig2–3'F.

SEQ ID NO: 15 is a Sandwich Hybridization Assay (S.H.A) *H. akashiwo* probe designated Het 1.25 aS.

SEQ ID NO: 16 is a S.H.A. *H. akashiwo* probe designated Het 1.25 bS.

SEQ ID NO: 17 is a S.H.A. *H. akashiwo* probe designated Het 3S.

SEQ ID NO: 18 is a S.H.A. *H. akashiwo* probe designated Het.sig2–3'F.

SEQ ID NO: 19 is a Raphidophyceae probe designated Raphid 1F.

SEQ ID NO: 20 is a Raphidophyceae probe designated Raphid 2F.

SEQ ID NO: 21 is a *F. japonica* probe designated Fib.1.25aS.

SEQ ID NO: 22 is a *F. japonica* probe designated Fib.sig3F.

SEQ ID NO: 23 is a *Chationella antiqua* probe designated Chat.1.25F/S.

SEQ ID NO: 24 is a *Chatuonella antiqua* 'D1, D2' domain LSU rDNA gene sequence.

SEQ ID NO: 25 is a *Chattonella subsalsa* 'D1, D2' domain LSU rDNA gene sequence.

SEQ ID NO: 26 is a *Fibrocapsa japonica* 'D1, D2' domain LSU rDNA gene sequence.

SEQ ID NO: 27 is a *Heterosigma akashiwo* 'D1, D2' domain LSU rDNA gene sequence.

SEQ ID NO: 28 is a *Vacuolaria virescens* 'D1, D2' domain LSU rRNA gene sequence.

SEQ ID NO: 29 is a PCR primer used to amplify the 'D1, D2' domain LSU rRNA gene designated DIR.

SEQ ID NO: 30 is a PCR primer used to amplify the 'D1, D2' domain LSU rRNA gene designated D2C.

DETAILED DESCRIPTION OF THE INVENTION

Unless defined otherwise herein, all technical and scientific terms used herein have the same meaning as commonly understood by one of ordinary skill in the art to which this invention belongs. Singleton et al., *Dictionary of Microbiology and Molecular Biology*, second edition, John Wiley and Sons, NY (I1994), and Hale and Marham, *The Harper Collins Dictionary of Biology*, Harper Perennial, NY (1991) provide one of skill with a general dictionary of many of the terms used in this invention. Although any methods and materials similar or equivalent to those described herein can be used in the practice or testing of the present invention, the preferred methods and materials are described. In order to more clearly understand the invention, the following specific definitions are provided:

Raphidophytes: Raphidophytes are algae of the class Raphidophyceae which includes *Heterosigma akashiwo, Fibrocapsa japonica, Chattonella antigua* and others (see Table 1 and C. Van Den Hoek, et. al. Algae, an introduction to phycology, Chapter 10 Heterokontophyta: Class Raphidophyceae, Cambridge University Press, Cambridge, 1995).

Oligonucleotide Probe: Oligonucleotide probes or polynucleotide probes include both double stranded and single stranded DNA or RNA. The probes may be synthesized synthetically or be recombinantly derived sequences. The probes include a specific oligonucleotide sequence and its complement sequence, e.g. A-T/U and C. G. Oligonucleotide probes include a single oligonucleotide sequence or a mixture of the given sequences, or a mixture of probes that may contain as a part of the probes single or multiple copies of the given oligonucleotide sequences.

Probe Compositions: Probe compositions include probes complementary to raphidophyte rRNA. The probes may be in a pure state or in combination with other probes. In addition, the probes may be in combination with salts or buffers, and may be in a dried state, in an alcohol solution as a precipitate, or in an aqueous solution. The probes may be a mixture of different probes capable of detecting a single species or two or more species, a mixture of different probes wherein the probes are each able to detect one or more species.

Open Regions: Open regions are regions of RNA which have minimal secondary or tertiary interactions with adjacent nucleotides.

Closed Regions: Closed regions are regions of RNA with significant secondary or tertiary interactions with adjacent nucleotides.

Homologous Sequences: Homologous sequences are sequences which have sufficient identity to another sequence such that under standard hybridization conditions of moderate stringency the percent hybridization can be shown to exceed 50% of the hybridization between perfectly complementary nucleic acid fragments. Homologous sequences for hybridization complexes between pairs of nucleotides.

Non Homologous Sequences: Non homologous sequences are sequences which have sufficient differences to another sequence that under standard hybridization conditions of moderate stringency the percent hybridization is less than 50% of the hybridization between perfectly complementary nucleic acid fragments.

Marine Sample: A marine sample is a specimen of sea water or of an organism living within the sea The term also encompasses a digestive tract specimen from an organism not necessarily living within, but taking nutrition exclusively from, the sea.

Permeabilize: Permeabilize means to disrupt a cell to allow for intracellular or extracellular hybridization between nucleic acid probes and rRNA. A permeabilized cell may be lysed to allow extracellular release of rRNA, fixed so as to allow entry of probes into the cell, or both rRNA is exposed when the rRNA is rendered accessible to hybridization by a complementary segment of nucleic acid.

Nucleotides: Nucleotides refer to deoxyribonucleotide or ribonucleotides. These nucleotides may be in the form of a polymer in either single- or double-stranded form as a nucleic acid, and unless otherwise limited, encompass known analogues of natural nucleotides that hybridize to nucleic acids in a manner similar to naturally occurring nucleotides.

Subsequence: The subsequence of a particular nucleic acid or polypeptide sequence refers to a region of the nucleic acid or polypeptide smaller than the particular nucleic acid or polypeptide.

Hybridization Wash Conditions: Hybridization wash conditions refer to those wash conditions for nucleic acid hybridization experiments such as Southern and northern hybridizations which are sequence dependent. In nucleic hybridization experiments, hybridization complexes are formed between homologous sequences. An extensive guide to the hybridization of nucleic acids is found in Tijssen, *Laboratory Techniques in Biochemistry and Molecular Biology—Hybridization with Nucleic: Acid Probes*, Part I, Chapter 2 "Overview of principles of hybridization and the strategy of nucleic acid probe assays", Elsevier, N.Y. (1993) which is hereby incorporated by reference. Stringency of the wash conditions are dependent on numerous factors including the temperature, components and other factors. Generally, highly stringent wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular probe.

Taking into account the above definitions, the present invention relates to compositions, methods and diagnostic kits for the detection of fish killing raphidophyte algae using RNA targeted probes. The probes comprise a segment of nucleic acid capable of selectively hybridizing, under selective hybridization conditions, to large-subunit ribosomal RNA from raphidophytes. The probes include those sequences selected from SEQ ID NO: 3 through SEQ ID NO: 23 and homologous sequences.

1. Probes

The probes of the present invention are generally of the formula:

[X-Y-Z]$_n$

In the formula, X is a sequence of 0 to 100 nucleotides or nucleotide analogs that are non-homologous to conserved or non-conserved regions of raphidophyte nucleic acid. Furthermore, Y is a sequence of 10 to 100 nucleotides or nucleotide analogs that are capable of hybridizing under hybridizing conditions to hypervariable regions of the ribosomal RNA of raphidophytes. Such nucleotides or nucleotide analogs include those sequences selected from SEQ ID NO: 3 through SEQ ID NO: 23.

In the formula, Z is a sequence of 0 to 100 nucleotides or nucleotide analogs that are non homologous to conserved or non conserved regions of raphidophyte nucleic acid. The sequence of Z may be the same or different from X Finally, n is 1–500 or more. In the probes where n is greater than 1, Y can be the same or different sequences of nucleotides having hybridization capability. The probe can be fee or contained within a vector sequence (e.g., plasmids, viruses or cosmids).

The nucleic acid sequence of the claimed probes include homologous synthetically derived or recombinant nucleic acid sequences which have sufficient identity with the claimed sequences that they substantially hybridize with regions complementary to the claimed probes to form hybridization complexes. By "substantially" it is meant that under standard hybridization conditions of moderate stringency, percent hybridization can be shown to exceed 50% of the hybridization between perfectly complementary nucleic acid fragments.

The probes of the present invention substantially bind under selective hybridizing conditions to regions of raphidophyte rRNA having minimal secondary or tertiary interactions with adjacent nucleotides known as open regions. By "substantially bind" it is meant that the probes do not comprise significant sequences that bind to regions that are available for hybridization only after heating, that is, regions with significant secondary and tertiary structure (closed regions). In practical terms, such probes will generally not comprise any more than 10 flanking nucleotides (either 5' or 3') which would bind to closed regions. More specifically, compositions of polynucleotide probes complementary to open regions are claimed that are complementary to either the hypervariable or, alternatively, to the conserved regions of rRNA of raphidophyte species.

The probes of the present invention may be compounds of RNA, DNA, or RNA/DNA chimeras. In the probes, analogs of nucleotides may be substituted for naturally occurring nucleosides. Nucleotide analogs offer greater stability, resistance to nuclease activity and ease of signal attachment. The term "probe" is intended to embrace all functionally equivalent sequences. Equivalent raphidophyte probes may also consist of the given sequence, concatemers of the sequence, or probes flanked by about 10 or less bases of any degree of complementarity to the native sequences flanking the complementary region of raphidophyte rRNA.

2. Probes Complementary to rRNA of Raphidophytes

The degree of complementarity (homology) required for detectable binding of probes of the present invention with the rRNA of raphidophytes will vary in accordance with the stringency of the hybridization medium and/or wash medium. The degree of complementarity will optimally be 100 percent; however, it should be understood that minor variations between the rRNA and the disclosed probes may still provide for selective hybridization to a particular rRNA without undesired cross-hybridization to other accessible nucleic acids in the sample. Such minor variations may be compensated for by reducing the stringency of the hybridization and/or wash medium as described below. Thus, despite the lack of look complementarity under reduced conditions of stringency, functional probes having minor base differences from their rRNA targets are possible. Therefore, under hybridization conditions of reduced stringency, it may be possible to slightly modify the disclosed probes while maintaining an acceptable degree of specificity to detect the desired raphidophyte species present in the sample.

3. Synthesis or Isolation of the Probes

The probes of the present invention may be chemically synthesized using commercially available methods and equipment. Methods of synthesizing nucleic acids are well known in the art. Deoxynucleotides may be synthesized chemically according to the solid phase phosphoramidite triester method described by Beaucage and Caruthers, *Tetrahedron Letts*. 22(20):1859–1862 (1981), e.g., using an automated synthesizer, e.g., as described in Needham-VanDevanter et al., *Nucleic Acids Res*. 12:6159–6168 (1984).

To obtain large quantities of oligonucleotide probes, one can also clone the desired sequence using traditional cloning methods, such as described in Maniatis, T., et al. *Molecular Cloning: A Laboratory Manual*, Cold Spring Harbor, N.Y. (1982), or one can produce the probes by chemical synthesis using commercially available DNA synthesizers. An example of cloning would involve insertion of the cDNA for the ribosomal RNA into a replication vector, such as pBR322, M13, or into a vector containing the SP6 promotor (e.g., generation of single-stranded RNA using SP6 RNA polymerase), and transformation of a bacterial host The DNA probes can be purified from the host cell by lysis and nucleic acid extraction, treatment with selected restriction enzymes, and further isolation by gel electrophoresis. The use of polymerase chain reaction (PCR) technology can also be used to obtain large quantities of probe. (See U.S. Pat. No. 4,683,202.)

4. Uses of the Probes

The probes of the invention are useful for detecting raphidophytes in a marine sample. The present invention is thus also directed to methods of detecting a raphidophyte species from a marine sample. These methods include the steps of: (a) permeabilizing the cells of the raphidophyte species to expose the ribosomal RNA; (b) contacting the ribosomal RNA under hybridizing conditions with polynucleotide probes capable of selectively hybridizing to a hypervariable or conserved region of the ribosomal RNA of species; and (c) detecting hybridization complexes as an indication of the presence of the species in the sample.

Marine samples for use in this invention can be obtained by any number of methods well known to the skilled artisan including tow samples of marine waters. The samples may be collected using an aquatic autosampler as described in applicant's co-pending U.S. patent application Ser. No. 09/319,333 entitled "Aquatic Autosampler" which is hereby incorporated by reference. The samples may be subsequently processed, for example, to remove precipitated material, or gently filtered to concentrate the sample or exclude organisms of particular size, or cultured to enrich or deplete the population of particular organisms. Conveniently, the sample is dispersed in a buffer protective of, or compatible with rRNA [Boney, A.D., *Phytoplankton, Studies in Biology*, no. 52 (1979)].

The sample, or a portion thereof, may be permeabilized for use in a sandwich hybridization assay in a lysis buffer such as disclosed in Van Ness et al., *Nucl. Acids. Res.* 19:5143–5151 (1991), and PCT application WO 93/24659, both incorporated herein by reference. Lysing solutions are well known in the art and are typically composed of a buffered detergent solution having a divalent metal chelator or a buffered chaotrophic salt solution containing a detergent (such as SDS), a reducing agent and a divalent metal chelator (EDTA). Generally, these buffers are between pH 7.0 and 9.0, and contain both chelating agents and surfactants.

Mechanical methods, including French press, nitrogen cavitation, bead beater, ultrasound sonification, and heating, may also be employed to permeabilize the cell. Alternatively, samples may be collected and dispersed in a lysing solution that also functions as a hybridization solution, such as 3M guanidinium thiocyanate (GuSCN), 50 mM Tris (pH 7-6), 10 mM EDTA, 0.1% sodium dodecylsulfate (SDS), and 1% mercaptoethanol [Maniatis, et al., *Molecular Cloning: A Laboratory Manual*, Cold Spring Harbor, N.Y. (1982)].

5. Hybridization Assays

The probes of the invention may be utilized to assay for raphidophytes using various hybridization assays. Assay test protocols for use in this invention are those of convention in the field of nucleic acid hybridization Assay test protocols include both single phase hybridizations, where the target and probe polynucleic acids are both in solution and mixed phase hybridizations, where either the target or probe polynucleotides are fixed to an immobile support. Mixed phase hybridizations include non-sandwich type assays. Whole cell hybridizations may also be employed using methods well known in the art and exemplified herein. The assay test protocols known to the skilled artisan are varied and are not to be considered a limitation of this invention.

Various hybridization solutions may be employed. Hybridization solutions generically include from about 20 to 60% volume, preferably 30%, of a polar organic solvent. A common hybridization solution employs about 5% v/v formamide, about 0.5 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, 0.01–0.051% Ficoll (about 300–500 kilodaltons), 0.01–0.05% polyvinylpyrrolidone (about 250–500 KDa), and 0.01–0.05% serum albumin. Also included in the typical hybridization solution will be unlabeled carrier nucleic acids from about 0.1 to 5 mg/ml, fragmented nucleic DNA, e.g., calf thymus or salmon spend DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polyrnethylacrylate, or polystyrene sulfonic acid and anionic saccharidic polymers, such as dextran sulfate.

An alternative hybridization solution may be employed including about 2 to 4M GuSCN, preferably 3M, about 0.01 to 0.1M Tris (pH range about 6.0 to 8.9), a detergent such as sodium dodecyl sulfate in concentrations of about 0.1 to 5% (wt./vol.), and about 0.01 to 0.1M EDTA. Other additives may also be included such as carrier DNA or RNA, or protein such as bovine serum albumin or gelatin. Stringency of the hybridization solution can be adjusted by the addition of about 0 to 10% formamide, usually 5%.

The particular hybridization technique utilized is not essential to the invention. Hybridization techniques are generally described in *Nucleic Acid Hybridization: A Practical Approach*, Ed. Hames, B. D. and Higgins, S. J., IRL Press (1987); Gall et al., *Proc. Natl. Acad. Sci., U.S.A.*, 63:378–383 (1969), and John et al. *Nature*, 223:582–587 (1969). As improvements are made in hybridization techniques, they can readily be applied.

Regardless of the assay test protocol being used, the raphidophyte cells or cell contents are to remain in contact with a hybridization solution for an extended period of time. In single phase assays, the double-stranded duplexes may be separated from single-stranded nucleic acid by $S_1$ nuclease digestion followed by precipitation of duplex molecules, or by selective binding to hydroxyapatite. In mixed phase assays, the support-immobilized nucleic acid is typically introduced into a wash solution having analogous concentrations of sodium chloride, buffers, and detergent, as provided in the hybridization solution. The time period for which the support is maintained in the wash solution may vary from several minutes to three hours or more.

The amount of labeled probe which is added to the hybridization solution may vary widely, depending upon the nature of the label, the amount of the labeled probe which can reasonably bind to the cellular target nucleic acid, and the stringency of the hybridization medium and/or wash medium. Generally, substantial excesses of probe over the stoichiometric amount of the target nucleic acid will be employed to enhance the rate of binding of the probe to the target DNA.

Various degrees of stringency of hybridization can be employed. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the Ad reactant solution through manipulation of the concentration of formamide within the range of 0% to 50%.

Either the hybridization or the wash medium can be stringent. Typically, for mixed phase assays, it is the wash solution that most often determines the stringency and facilitates dissociation of mismatched duplexes. After rinsing the support at room temperature with a dilute buffered sodium chloride solution, the support may now be assayed for the presence of duplexes in accordance with the nature of the label.

In F.I.S.H. assays cells are fixed, treated with hybridization buffer and then hybridized with probe as described in the Example section below. The cells are then analyzed by epifluorescence microscopy.

In a sandwich-type assay a primary component is a solid support The solid support has absorbed to it or covalently coupled to it immobilized nucleic acid probe that is unlabeled and complementary to one portion of the rRNA sequence. Probes hybridize to regions of the ribosomal RNA with minimal secondary and tertiary interactions. The advantage of such probes is that the hybridization can be carried out without the additional step of heat denaturing the sample nucleic acid. For the sandwich-type assay, the test sample suspected of containing one or more raphidophytes is contacted with the solid support in a hybridization medium. In the procedure, a second 6soluble-labeled probe complementary to a different sequence of the rRNA of the raphidophyte is hybridized to the rRNA that has formed a hybridization duplex with the immobilized nucleic acid probe on the solid support. A probe to a hypervariable region and a probe to a conserved region of rRNA of raphidophyte may each function as either a capture or signal probe. The entire assay takes place at 30° C.

The presence of raphidophyte species assayed from the marine sample is then determined in accordance with the label being used. It should be noted that in sandwich hybridization assays the second probe can be added simultaneously with the test sample to the hybridization assay. In addition, the second probe can hybridize to either a conserved or to a hypervariable region of the rRNA.

Compared to the whole cell F.I.S.H method, sandwich hybridization is several fold faster and far less taxing on the individual executing the protocol [Scholin, C. A., et al. DNA probes and a receptor-binding assay for detection of *Pseudo-nitzschia* (Bacillariophyceae) species and domoic acid activity in cultured and natural samples. J. Phycol. 35: 1356–1367 (1999)]. Equipment used to apply this method includes a standard filtration manifold, heating block, micro pipette, and a robotic processor. The latter costs several thousand dollars less than an average epifluorescence microscope and is available commercially. It is possible to apply this method outside of a laboratory. Using current technology, the lower limit of detection (LLD) for sandwich hybridization is roughly $2.5–5\times10^2$ raphidophyte cells 0.2 $ml^{-1}$ of lysate. For whole water samples, it is possible to detect as few as several hundred to $10^3$ cells $1^{-1}$ using the current sandwich hybridization assay and instrumentation described above.

6. Detection of Raphidophytes

Various detection labels may be utilized. Where the label is radioactive, the presence of probe can be detected in a scintillation counter. More conveniently, in mixed phase assays, the substrate can be dried and exposed to X-ray film in any number of conventional autoradiographic protocols. Autoradiographic detection is typically employed with $^3H$, $^{125}I$, $^{35}S$, $^{14}C$, or $^{32}P$ labeled probes or the like. The choice of radioactive isotope depends on research preferences due to ease of synthesis, stability and half lives of the selected isotopes.

Where the label is fluorescent, the sample is detected by first irradating it with light of a particular wavelength. The sample absorbs this light and then emits light of a different wavelength which is picked up by a detector.

Where the label is a hapten or antigen, the sample can be detected by using antibodies. In these systems, a signal is generated by attaching fluorescent or enzyme molecules to the antibodies; in some cases the antibody is labeled with a radioactive probe as described in Tijssen, P., *Practice and Theory of Enzyme Immunoassays, Laboratory Techniques in Biochemistry and Molecular Biology*, Burdon, R. H., van Knipperberg, Ph.H., Eds., Elsevier, pp. 9–20 (1985), which is hereby incorporated by reference.

One method of detection is enzymatic detection in conjunction with biotin. Although fluorescence is an alternative label, enzymatic labels, in combination with avidin or streptavidin such as biotinylated peroxidase or alkaline phosphatase, are preferred. Enzyme conjugated avidin or streptavidin can also be used to directly bind the enzyme to the probe. Preferred enzymes are peroxidase or alkaline phosphatase.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, [Renz, et al., *Nuc. Acids Res.* 12:3435–3444 (1984)] and synthetic olignucleotides have been coupled directly with alkaline phosphatase [Jablonski et al., *Nuc. Acids. Res.* 14:6115–6128 (1986)]. A general reference for various detection methods can be found in Hames, B. D. and Higgins, S. J., *Nucleic Acid Hybridization*, IRL Press, Oxford (1985). References for sandwich assay with DNA probes are Dunn and Hassell, *Cell*, Vol. 12, pp. 23–26 (1977), and Ranki, et al., U.S. Pat. No. 4,486,539. All of these articles are hereby incorporated by reference.

7. Kits

The oligonucleodde or polynucleotide acid probes of this invention can be included in a kit which can be used to rapidly determine the presence or absence of raphidophyte species from a marine sample. The kit includes all components necessary to assay for the presence of these species.

The kit includes a stable preparation of rRNA probes, hybridization solution in either dry or liquid form for the hybridization of target and probe polynucleotides, as well as a solution for washing and removing undesirable and non-duplexed polynucleotides, and a substrate for detecting the labeled duplex. The probes may be labeled or unlabeled. The kit will also include directions for using the probes.

A more specific embodiment of this invention embraces a kit that utilizes the concept of the sandwich hybridization assay (S.H.A.). This kit would include as a first component, vials for containment of a marine sample and buffers for the permeabilization of the sample. A second component would include media in either dry or liquid form for the hybridization of target and probe polynucleotides, as well as for the removal of undesirable and nonduplexed forms by washing. A third component includes a solid support (such as a dipstick) upon which is fixed or to which is conjugated unlabeled nucleic acid probe(s) that is (are) complementary to a part of the rRNA of the species assayed for. In the case of multiple target analysis more than one capture probe, each specific for its own ribosomal RNA, will be applied to different discrete regions of the dipstick. A fourth component would contain a labeled or unlabeled probe that is complementary to a second and different region (conserved or hypervariable) of the same rRNA strand to which the immobilized, unlabeled nucleic acid probe of the third component is hybridized.

The probe components described herein include coordinations of probes in dry form, such as lyophylized nucleic acid or in precipitated form, such as alcohol precipitated nucleic acid or in buffered solutions. The various reagents for the detection of labeled probes and other miscellaneous materials for the kit, such as instructions, positive and negative controls, and containers for conducting, mixing, and reacting the various components, would complete the assay kit. Such kits would include instruction cards and vials containing the various solutions necessary to conduct a nucleic acid hybridization assay. These solutions would include lysing solutions, hybridization solutions, combination lysing and hybridization solutions, and wash solutions. The kits would also include labelled probes. Standard references for comparison of results may also be provided for an easy estimate of the number of raphidophyte species in a given solution. Depending upon the label used additional components may be needed for the kit, e.g., enzyme labels require substrates.

From the foregoing description it will be clear to those of skill in the art that the disclosed probes are useful for identifying raphidophytes collected from pure cultures or nature. Moreover, the technique offers promising means by which one could quantify these species rapidly. The protocol is neither extremely complicated or demanding, and with minimal training all individuals should be able to execute both methods.

The invention is now illustrated by way of the following non-limiting examples.

EXAMPLES

Example 1

Algae Cultures

The algae cultures utilized to isolate the probes of this invention are listed in Table 1. All cultures are currently held at the Cawthron Institute, Nelson, New Zealand (K. Ponikla). Cultures are maintained under a 12:12 light/dark photoperiod at 20° C. in f/2 media (Guillard, R. R. L. 1975. Culture of phytoplankton for feeding marine invertebrates. In: *Culture Of Marine Invertebrate Animals* (ed. by W. L. Smith & M. H. Chanley), pp. 29–60, Plenun Press, New York.).

TABLE 1

Species probed in this study and culture collection numbers.

| Species | Class | Culture collection number |
| --- | --- | --- |
| *Chattonella antiqua* | Raphidophyceae | CAWRO1 |
| *Chattonella subsaisa* | Raphidophyceae | CCMP217 |
| *Fibrocapsa japonica* | Raphidophyceae | CAWRO2, O3 |
| *Heterosigma akashiwo* | Raphidophyceae | CAWRO4, O5, O6, O9, 14(ABC2) |
| *Heterosigma* sp. | Raphidophyceae | CAWR10 |
| *Olisthodiscus luteus* | Uncertae sedis | NIES-15 |
| *Nannochloropsis oculata* | Eustigamatophyceae | LB2164 |

*Notes on Table 1:
CAW
Cawthron Institute, Nelson, New Zealand, Algal Collection
CAW14(ABC$^2$) was provided by Dr. Rita Horner, University of Washington, Seattle, Washington, USA.
CCMP Provasoli-Guillard National Centre for Culture of Marine Phytoplankton, West Boothbay Harbor, Maine, USA
LB The University of Texas of Austin, Austin, Texas, USA, Culture Collection of Algae
NIES National Institute for Environmental Studies, Japan, Microbial Culture Collection, City, Japan

Example 2

DNA Extraction

Cells from Example 1 grown to mid-log phase growth were harvested by centrifugation Approximately 10 mg of algal cells was added to 700 μL of CTAB buffer (50 mM Tris pH 8.0, 0.7M NaCl, 10 mM EDTA, 1% CTAB). 1 μL of 0.1% of β-mercapto-ethanol was then added and the mixture vortexed to resuspend the pellet. After the pellet had been resuspended 30 μL of 20 mg.mL$^{-1}$ Proteinase K was added, gently mixed, then incubated at 60° C. for 1 hour. If the pellet was still intact after 1 hour a further 5 μL of Proteinase K was added and incubated for another hour. After the incubation an equal volume of 24:1 chloroform:isoamyl alcohol was added, vortexed and placed on a shaker for 5 minutes. The mixture was then centrifuged at 13,000 rpm for 5 minutes at 4° C. and the supenatant transferred to a new tube. An equal volume of 25:24:1 phenol:chloroform:isoamyl alcohol was added, vortexed and placed on a shaker for 5 minutes. The mixture was then centrifuged at 13,000 rpm for 5 minutes at 4° C. and the supernatant transferred to a new tube. This step was continued until the interphase was clear. Another 24:1 chloroform:isoamyl alcohol extraction was then done as for the first step and the supenatant transfer to a new tube. An equal volume of isopropanol was added to the supenatant, mixed and placed at −20° C. for at least an hour. The DNA was pelleted by centrifugation at 13,000 rpm at 4° C. for 30 minutes, then washed 2 times with 70% ethanol, using a 5 minute centrifugation step at 13,000 rpm at 4° C. The DNA pellet was dried under vacuum and resuspended in 50 μL of ddH$_2$O.

Example 3

PCR Amplification

Amplification of DNA from Example 2 was achieved using the polymerase chain reaction (PCR). The following primers were used to amplify the 'D1, D2' domain LSU rDNA gene:

DIR (forward)5' ACC CGC TGA ATT TAA GCA TA 3'
(SEQ ID NO: 29)
D2C (reverse) 5' CCT TGG TCC GTG TTT CAA GA 3'
(SEQ ID NO: 30)

The primers are targeted at conserved regions at positions 24–45 for DIR and 733–714 for D2C, relative to the *Prorocentrium micans* LSU rRNA gene sequence. Approximately 10 ng of genomic DNA was added to a PCR mix containing 0.25 mM dATP, 0.25 mM dCTP, 0.25 mM dGTP, 0.25 mM dTTP, 2.5 mM $MgCl_2$, 50 mM KCl, 50 ng of each primer, 1.25 units of Taq polymerase (AmnpliTaq™) polymerase and sterile water to a final volume of 50 µL. A DNA thermal cycler was used to subject the reaction to an initial cycle of denaturation (Hot Start, 94° C. for 3 minute), and then 15 cycles of denaturation (94° C. for 30 seconds), annealing (60° C. each round for 30 seconds) and extension (72° C. for 1 minute). These initial cycles were followed by 15 more rounds of denaturation (94° C. for 30 seconds), annealing (55° C. for 30 seconds) and extension (72° C. for 1 minutes) and a final extension of 7 minutes. To check PCR fragment size and purity, 5 µL of PCR product was run out on a 0.8% agarose gel, stained with ethidium bromide and viewed on a UV transilluminator.

Example 4
Automated DNA Sequencing

Sequencing reactions were carried out using an ABI 373A 'stretch' automated sequencer. Both the coding and noncoding strands were sequenced from a pooled PCR product (at least 2 PCR reactions) from Example 3, using the PCR primers in dye terminator reactions. The sequences were checked and corrected with the SEQED and gelassemble programs, using the sequence electrophoretogram for visual assurance (Genetics Computer Group. 1994. *Program manual for GCG package, Version* 8. Wisconsin, USA).

Example 5
Probe Design and Synthesis

The D1 and D2 domains of the LSU rRNA gene (D1, D2 LSU rRNA) were sequenced (SEQ ID NO:24–28) to provide information for the design of species-specific rRNA-targeted oligonucleotide probes and to construct a phylogenetic framework for intra-class organization of the Raphidophyceae. The rRNA gene transcript contains a mosaic array of conserved and hypervariable domains, which provide unique nucleotide 'signatures' that allow the design of oligonucleotide probes which can be diagnostic from Kingdom to species or even strain-specific levels. Oligonucleotide probes generally are targeted at rRNA because the high copy number present in cells offers a naturally amplified target for probe localization.

Species-specific oligonucleotide probes were designed by looking for unique 'signatures' in the alignment and aiming for a 50% GC content with a probe/target melting temperature (Tm) of between 60° C. and 75° C. depending on the application. The initial oligonucleotide probes were then analysed by the program OligoTech, version 1.0 (Oligos Etc., Eugene, Oreg.) to check for intramolecular folding and/or homodimer problems and adjusted as required. These oligonucleotide probes were synthesized commercially with either a fluorescein or biotin moiety coupled to the 5' end (Oligos Etc., Eugene, Oreg., USA). The probes were resuspended in $ddH_2O$ at a concentration of 250 ng $µL^{-1}$, pipetted to multiple 0.6 mL tubes, then vacuum desiccated and stored at −80° C. Working stocks were resuspended in TE buffer (10 mM Tris HCl, 1 mM EDTA, pH 7.4) at a final concentration of 250 ng $µL^{-1}$ for F.I.S.H. probes and 100 ng $µL^{-1}$ for the S.H.A.

An oligonucleotide probe (Chat1.25F/S) has been successfully developed for *Chationella* spp. which displays good sensitivity and specificity in fluorescent in situ hybridization assays. The design of the probe was based on the sequences from the D1, D2 domains of the large subunit rRNA (LSU rRNA) gene for *Chauonella subsalsa* and *C. antiqua* (the *C. antiqua* gene sequence is homologous for the species *C. marina* and *C. ovata*) and an alignment of raphidophyte sequences. The probe Chat1.25F/S is in the same general position within the LSU rRNA gene as the probes for *Heterosigma akashiwo* (Het1.25aS) and *Fibrocapsa japonica* (Fib1.25S). The addition of an assay for Chattonella species completes the coverage of probes for species from the Raphidophyceae which are known to cause mortality of caged fish.

The sequences were aligned, revealing several unique species-specific nucleotide sequences and from these unique regions we designed a suite of oligonucleotide probes for *Heterosigma akashiwo, Fibrocapsa japonica, Chattonella* and raphidophytes in general. The oligonucleotide sequences are shown (SEQ ID NO: 1–23) in Table 2.

TABLE 2

Oligonucleotide probe sequences, targets and labels

| Probe | Target Species | Sequence and label type (5'-3') | SEQ ID NO: |
|---|---|---|---|
| UniC | positive control | Fluorescein-GWATTACCGCGGCKGCTG | 1 |
| uniR | negative control | Fluorescein-CAGCMGCCGCGGTAATWC | 2 |
| Het1.25F | H. akashiwo | Fluorescein-CGACTGAGCACGCACCTTT | 3 |
| Het1.5F | H. akashiwo | Fluorescein-GCGACGGCAAAAAGACCAGGA | 4 |
| Het2aF | H. akashiwo | Fluorescein-GCATGTTGAAACGCTCCAG | 5 |
| Het3F | H. akashiwo | Fluorescein-AGCAAAGGTCCTCCGTCCTA | 6 |
| Het.sig2-3'F | H. akashiwo | Fluorescein-TACTCTCTTTTCAAAGTCTTTTCATC | 7 |
| Raphid1F | Raphidophyceae | Fluorescein-CCGCTTCACTCGCCGTTACTAG | 8 |
| Raphid2F | Raphidophycaea | Fluorescein-TCATCTTTCCCTCACGGTACTTGTT | 9 |
| Fib1.25aF | F. japonica | Fluorescein-CGGCTGGACACGCTTCTGT | 10 |
| Fib1.5F | F. japonica | Fluorescein-CAGCACGAAATATGACCCCCG | 11 |
| Fib2F | F. japonica | Fluorescein-CCATGGGACACAGCGCGCACTAC | 12 |
| Fib3F | F. japonica | Fluorescein-TACAAACCAAGGTGCACTAATG | 13 |
| Fib.sig2-3'F | F. japonica | Fluorescein-AACTCTCTTTCCAAAGTTCTTTTCATC | 14 |
| Het1.25aS | H. akashiwo | Biotin-ACCACGACTGAGCACGCACCTTT | 15 |

TABLE 2-continued

Oligonucleotide probe sequences, targets and labels

| Probe | Target Species | Sequence and label type (5'-3') | SEQ ID NO: |
|---|---|---|---|
| Het1.25bS | H. akashiwo | Biotin-AGCCCGGGACCACGACTGAG | 16 |
| Het3S | H. akashiwo | Biotin-GAGCAAAGGTCCTCCGTCCTAAC | 17 |
| Het.sig2-3'F | H. akashiwo | Fluorescein-TACTCTCTTTTCAAAAGTCTTTTCATC | 18 |
| Raphid1F | Raphidophycaea | Fluorescein-CCGCTTCACTCGCCGTTACTAG | 19 |
| Raphid2F | Raphidophycaea | Fluorescein-TCATCTTTCCCTCACGGTACTTGTT | 20 |
| Fib1.25aS | F. japonica | Biotin-CGGCTGGACACGCTTCTGTAG | 21 |
| Fib.sig3F | F. japonica | Fluorescein-AACTCTCTTTCCAAAGTTCTTTTCATC | 22 |
| Chat1.25F/S | Chattonella spp. | (Fluorescein/Biotin*)-AGAGTAGCTGAGCACGCATCTCT | 23 |

*Fluorescein or Biotin label

Example 6
Screening of Candidate Probes

Initial screening of probes was conducted at approximately 10° C. below the Tm (melting temperature) and varied according to the degree of specificity required using Fluorescent In Situ Hybridization (F.I.S.H.). This initial hybridization temperature gives a good indication of probe accessibility to target rRNA and the signal intensity. In this study, the specificity of the F.I.S.H. reaction was controlled by the hybridization temperature, not the wash temperature and/or salt concentration.

The relative signal intensity of the species-specific and raphidophyte-specific probes spanning the D1, D2 rRNA gene were compared against a positive control probe (UniC) and a negative control probe (UniR) (SEQ ID No. 1–2). The positive control probe is targeted at universally conserved sequence of the small subunit rRNA gene (SSU rRNA) and should bind to the SSU rRNA of all organisms. The negative control probe is the complement of UniC and does not bind to any known rRNA target and therefore helps to determine the level to which probe retention is non-specific.

Approximately 5–10 mL of mid-exponential culture, net tow or whole (unconcentrated) seawater sample was pipetted gently into a 50 mL polypropylene, conical bottom, disposable centrifuge tube containing an ethannol/saline fixative. ((2 mL ddH$_2$O, 3 mL 25×SET buffer (3.75 M NaC1.25 mM EDTA, 0.5 M Tris HCI, pH 7.8) and 25 mL of 95% ethanol)). The mixture was left to stand at room temperature for at least 15 minutes before gently mixing by inversion, then allowed to stand an additional hour. Aliquots of the samples were filtered onto either 13 mm diameter, 1.2 $\mu$m pore size Isopore (Millipore) or Cyclopore (Whatman) polycarbonate membranes in a custom filter tube (Miller P. E. & Scholin C. A. 1998. Identification and enumeration of cultured and wild Pseudo-nitzschia (Bacillariophyceae) using species-specific LSU rRNA-targeted fluorescent probes and filter-based whole cellhybridization. J. Phycol. 34: 371–382). The filtered samples were washed with 1 mL of 5×SET hybridization buffer (5×SET, 0.1% v/v Igepal, 10 $\mu$gml$^{-1}$ poly A, Sigma), then resuspended in 0.5 mL 5×SET hybridization buffer, to which probe was added at a final concentration of 5 ng$\mu$L$^{-1}$. The filter manifold was then transferred to either a dark dry incubator or water bath for 30 min at 50° C. After the incubation, the excess probe was removed by washing with 1 mL of 5×SET buffer at room temperature for 2 min to remove excess unbound probe. The filters were then removed from the manifold and mounted on glass slides, sample side up, covered with 20 $\mu$L of Slow-Fade Light (Molecular Probes, Eugene, Oreg.) and then mounted with cover slips. Samples were examined by epifluorescence microscopy using a Zeiss Axioskop fitted with a fluorescein band-pass filter set (excitation 465–495 nm; dichoric 505 nm; emission 515–555 nm) and Olympus 10AD 35 mm camera system.

The relative signal intensity of the putative species and raphidophyte-specific LSU rRNA-targeted probes were compared against positive (UniC) and negative (UniR) control probes (Table 3). Cell staining intensity was scored visually using the criteria of Miller and Scholin (Miller P. E. & Scholin C. A. 1996. Identification of cultured Pseudo-nitzschia (Bacillariophyceae) using species-specific LSU rRNA-targeted fluorescent probes. J. of Phycol. 32: 646655.): cells with signal intensity similar to the positive control were scored as ++, signal intensity equivalent to the negative control was scored as --, and signal intensities clearly above the negative but below the positive control as +-. All F.I.S.H. probes were applied to log phase cultures of H. akashiwo, F. japonica and Chatoneila spp.

A preliminary screening of oligonucleotide probes using the F.I.S.H. assay was performed and the results are presented in Table 3. The positive control probe gave a clear and strong signal for all species examined. Furthermore, there was no non-specific retention of the negative control probe.

Of the probes tested, three putative species-specific probes for Heterogma akashiwo (Het1.25F, Het3F and Het. sig.2–3'F) and Fibrocapsa japonica (Fib1.25aF, Fib2F and Fib. sig.2–3'F) gave signal which was equivalent to the positive control. The Chat1.25F also labeled its target species with intensity similar to positive control. Both raphidiophyte signal probes (Raphid1F & 2F) gave signals which were comparable to the positive control. From these results, the probes which generated good signal were further tested for specificity against a range of isolates for the target species as well as non-target species, The results for this analysis are presented in Table 4.

TABLE 3

Preliminary screening of oligonucleotide probes using fluorescent in situ hybridization (F.I.S.H.) assays. Cross-specificity of probes was not tested in the initial screening.

| | Oligonucleotide probes | | | | | | | | | | | | | | |
|---|---|---|---|---|---|---|---|---|---|---|---|---|---|---|---|
| Species | Het 1.25F | Het 1.5F | Het 2aF | Het 3F | Het.sig 2-3'F | Fib 1.25F | Fib 1.5F | Fib 2F | Fib 3F | Fib.sig 2-3'F | Chat 1.25F | Raphid 1F | Raphid 2F | UniC | UniR |
| H. akashiwo | ++ | -- | +- | ++ | ++ | n/a | n/a | n/a | n/a | n/a | -- | ++ | ++ | ++ | -- |
| F. japonica | n/a | n/a | n/a | n/a | n/a | ++ | +- | ++ | -- | ++ | -- | ++ | ++ | ++ | -- |
| Chattonella | n/a | n/a | n/a | n/a | n/a | n/a | n/a | n/a | n/a | n/a | ++ | ++ | ++ | ++ | -- |

TABLE 4

Specificity and sensitivity of probes using the F.I.S.H. assays.

| | Probes | | | | | | | | | | |
|---|---|---|---|---|---|---|---|---|---|---|---|
| Species | Positive control | Negative control | Het1.25F | Het3F | Het.sig2-3'F | Fib1.25aF | Fib2F | Fib.sig2-3'F | Chat 1.25F | Raphid1F | Raphid2F |
| H. akashiwo | ++ | -- | ++ | ++ | ++ | +- | -- | +- | -- | ++ | ++ |
| Heterosigma sp. | ++ | -- | ++ | ++ | ++ | +- | -- | +- | -- | ++ | ++ |
| F. japonica | ++ | -- | +- | -- | +- | ++ | ++ | ++ | -- | ++ | ++ |
| C. antiqua | ++ | -- | +- | -- | +- | +- | -- | +- | ++ | ++ | ++ |
| C. subsalsa | ++ | -- | +- | -- | +- | +- | -- | +- | ++ | ++ | ++ |
| O. luteus | ++ | -- | -- | -- | -- | -- | -- | -- | -- | +- | +- |
| N. oculata | ++ | -- | -- | -- | -- | -- | -- | -- | -- | +- | +- |

*additional new data

The F.I.S.H. analyses gives an indication of binding sites for probes in the sandwich hybridization assay, but does not necessarily predict what combination of probes are best with respect to sensitivity and specificity. Previous experience has also shown that these combinations have to be determined empirically (Scholin C. A., Miller P. E., Buck K. R., Chavez, F. P., Harris, P., Haydock, P., Howard, J., Cangelosi G. 1998. Detection and quantification of *Pseudo-nitzschia australis* in cultured and natural populations using LSU rRNA-targeted probes. *Limnol. Oceanogr.* 42: 1265–1272: Scholin unpublished work). The probes Het1.25F and Het 3F were chosen for the capture probes and the fluorescein labels were exchanged for a biotin label. An alternative probe, Het 1.25bS, was also constructed to try and improve the specificity of Het1.25F which gave a weak signal when probed against other raphidophyte species in the F.I.S.H. format. Het 1.25F is equivalent to Het1.25aS where the fluorescein label has been exchanged for biotin. The probes Het. sig2F, Raphid1F and Raphid2F were chosen for the signal probes and these probes were constructed with a fluorescein label.

Example 7
A Sandwich Hybridization Assays

Candidate probes were designed for the sandwich hybridization assay (S.H.A.) after screening the LSU rRNA gene with probes in a F.I.S.H. format as described in Example 6. Probes which displayed good specificity and sensitivity in the F.I.S.H. analyses were redesigned for the higher Tm requirements of the sandwich hybridization assay, with biotin labels being attached for capture probes and fluorescein for the signal probes.

The sandwich hybridization assay utilized two probes. The first probe was a biotinylated species-specific capture probe, which was bound to a solid strepavidin-coated support The capture probe then bound with target rRNA molecules and was transferred to a second solution containing a fluorescein-labelled signal probe, thus forming the sandwich hybrid configuration. The hybrids were detected by a secondary-labelling reaction involving anti-fluorescein antibody conjugated to horseradish peroxidase that reacts with substrate to produce a blue colorimetric product. The intensity of the blue product is related to the number of rRNA molecules in the sandwich hybrid format, and from the number of rRNA molecules, it is possible to infer the number of algal cells present from a standard curve.

Samples for analysis with the S.H.A. were prepared as follows. Cultured cells and field samples were collected by gentle filtration onto 25 mm hydrophilic Durapore membranes (0.65 µM pore size, Millipore). The filters were transferred to filter tubes (Porex, Fairbum, Ga.) containing 400 µL of lysis buffer [(50 mM glycine, 10 mM EDTA, 5% N-lauryl sarcosine, 0.5% ProClin 150 (Rohm and Haas, Philadelphia), pH 11)], vortexed gently, then heated at 85° C. for 5 min, with an additional vortex after 2.5 min of incubation. After the incubation, 600 µL of hybridization buffer (100 mM Tris, 17 mM EDTA, 8.35% formarnide, 5 M guanidine thiocyanate, pH 7.5) was added to tubes in heat block. The tubes were removed immediately, vortexed gently and allowed to cool for 5 min. The tubes were then capped with a filter tip (1 µM pore size), or transferred to a syringe, coupled to a 0.45 µM Durapore Millex filter unit (Millipore) to remove particulate material from the crude cell lysate. The cell lysates were either allowed to cool to room temperature (~5 min) then were processed immediately, or they were placed into a −80° C. freezer for later analysis.

All hybridization steps were carried out using a portable robotics workstation which transfers a polystyrene strepavidin-coated strip with 12 prongs through each row of a standard 96-well microtiter plate (Saigene, Redmond, Wash.). Each row of the microtiter plate represents a different hybridization step. Assay development plates, which have ill the reagents for the S.H.A., except for probes and samples, were provided by Saigene (Redmond, Wash.). Filtered cell lysate (200 µL) was added to 3–4 wells for each sample, plus 2–3 wells for a negative control. The negative control probes do not bind to any known rRNA molecule, and serve as a procedural control to ensure that observed color development is specific to the capture/lysate/signal probe sandwich hybrid. The last well in the sample row was loaded with lysis/sample buffer. This well and the column serve as a chemistry-positive control, which utilises an oligonucleotide linker which forms a sandwich hybrid with the capture and signal probes.

After loading the samples into the wells, the microtiter plate was transferred to the temperature-controlled surface of the portable robotics workstation. The hybridzation steps were carried out at 30° C. and the entire run was completed in approximately 50 min. Each of the hybridization steps was completed with agitaion of the prongs in an up and down motion in well. Primary hybridization reactions, where the biotinylated capture probes are bounded to the strepavidin-coated prong, took place in 200 µL of Assay Wash buffer (Saigene, Redmond, Wash.), with capture probe at a final concentration of 200 ng $µL^1$ for 10 min. The prong/capture probe hybrids were transferred to the sample wells and secondary hybridization was allowed to proceed for 10 min. After the secondary hybridization reaction, the prong/capture probe/analyte hybrids were transferred into wells containing 175 µL of Signal Buffer (Saigene, Redmond, Wash.), with signal probe at a final concentration of 300 ng $µL^1$ for 8 min. At the completion of the tertiary hybridization step, the 'sandwich' hybrid (capture probe/analyte/signal probe) formation was complete. The sandwich hybrids were washed with 200 µL of Assay Wash solution (Saigene, Redmond, Wash.) for 2 min. Then the prong/sandwich hybrids were placed into 200 µL of anti-fluorescein-horseradish peroxidase (HRP) conjugate for 10 min. The prongs were then rinsed twice for 2 min as described above. The final step was the incubation of prong/sandwich hybrids in 200 µL of HRP substrate (TMB) for 12 min to allow color development At the completion of the run, the microtiter plate was quickly transferred into a plate reader and the absorbance was measured at 655 nm. The plate was removed and 50 µL of 10% (v/v) sulphuric acid was added for color enhancement. The plate was transferred back into the microtiter plate reader and the absorbance was measured at 450 nm. All reagents for the S.H.A. are available from Saigene Corp. under the trade names listed above (Redmond, Wash.).

The sensitivity and cross-reactivity tests on cultured isolates for *Heterosigma akashiwo* revealed that the probe combination Het1.25aS/Raphid1F provided the best signal, and no cross-reactivity has been observed. It was expected that there may be some cross-reactivity with the Het1.25aS probe based on the observations of the probe Het1.25aF in the F.I.S.H. analyses. The higher stringency and the lengthening of the probe for the S.H.A. appears to have eliminated these potential problems. It is well known that a small shift in a probe's position can have dramatic effects on the signal output. The probe Het1.25bS which was shifted a few bases towards the 5' end of the LSU rRNA gene, and which still included numerous bases of the probe Het1.25aS had a significantly reduced signal output in the S.H.A in comparison to the Het1.25aS/Raphid1F probe combination. The results for the sandwich hybridization assays for the probe combination matrix are described in Table 5.

TABLE 5

Sandwich hybridization probe matrix showing the combination and position of probes, and the signal output at 450 and 655 nm.

| Probe Combination | Target Species[b] | Probe Positions 5' end[a] | OD @ 450 nm ±SD | OD @ 655 nm ±SD |
|---|---|---|---|---|
| Het1.25aS (SEQ ID NO: 15)/Raphid1F (SEQ ID NO: 8) | *H. akashiwo* | 149/79 | 1.595 ± 0.209 | 0.768 ± 0.091 |
| Het1.25aS (SEQ ID NO: 15)/Raphid2F (SEQ ID NO: 9) | *H. akashiwo* | 149/344 | 0.0633 ± 0.006 | 0.058 ± 0.003 |
| Het1.25aS (SEQ ID NO: 15)/Het.sig2-3'F (SEQ ID NO: 7) | *H. akashiwo* | 149/366 | 0.0773 ± 0.006 | 0.063 ± 0.002 |
| Het1.25bS (SEQ ID NO: 16)/Raphid1F (SEQ ID NO: 8) | *H. akashiwo* | 157/79 | 0.583 ± 0.081 | 0.307 ± 0.040 |
| Het1.25bS (SEQ ID NO: 16)/Raphid2F (SEQ ID NO: 9) | *H. akashiwo* | 157/344 | 0.094 ± 0.048 | 0.073 ± 0.024 |
| Het1.25bS (SEQ ID NO: 16)/Het.sig2-3'F (SEQ ID NO: 7) | *H. akashiwo* | 157/366 | 0.054 ± 0.003 | 0.054 ± 0.002 |
| Het3S (SEQ ID NO: 17)/Raphid1F (SEQ ID NO: 8) | *H. akashiwo* | 567/79 | 0.093 ± 0.009 | 0.068 ± 0.003 |
| Het3S (SEQ ID NO: 17)/Raphid2F (SEQ ID NO: 9) | *H. akashiwo* | 567/344 | 0.222 ± 0.011 | 0.128 ± 0.002 |
| Het3S (SEQ ID NO: 17)/Het.sig2-3'F (SEQ ID NO: 7) | *H. akashiwo* | 567/366 | 0.080 ± 0.016 | 0.080 ± 0.016 |

TABLE 5-continued

Sandwich hybridization probe matrix showing the combination and position of probes, and the signal output at 450 and 655 nm.

| Probe Combination | Target Species[b] | Probe Positions 5' end[a] | OD @ 450 nm ±SD | OD @ 655 nm ±SD |
|---|---|---|---|---|
| Fib1.25aS (SEQ ID NO: 21)/Raphid1F (SEQ ID NO: 8) | F. japonica | 122/49 | 1.32 ± 0.040 | 0.634 ± 0.020 |
| Fib1.25aS (SEQ ID NO: 21)/Raphid2F (SEQ ID NO: 9) | F. japonica | 122/322 | 0.094 ± 0.009 | 0.067 ± 0.004 |
| Fib1.25aS (SEQ ID NO: 21)/Fib.sig2-3'F (SEQ ID NO: 14) | F. japonica | 122/344 | 0.087 ± 0.006 | 0.067 ± 0.004 |

[a]Ribosomal RNA complement. Aligned position with respect to target sequence.
[b]The clones used for this analysis are CAWR05 FOR *Heterosigma akashiwo* and CAWR03 for *Fibrocapsa japonica*. Refer to Table 1 for details about these clones.

The best combinations of probes for signal production in *Heterosigma akashiwo* and *Fibrocapsa japonica* were the Het1.25a capture probe (SEQ ID NO: 15)/Raphid1F signal probe (SEQ ID NO:8) and Fib1.25a capture probe (SEQ ID NO:21)/Raphid1 F signal probe (SEQ ID NO:8) respectively. These combinations of probes were used in all the following analyses.

Also, the S.H.A. probes were modified from the F.I.S.H. probes due to the higher Tm requirement and this may affect the signal output and specificity. A probe matrix was used to test all possible combinations of capture and signal probes for signal production. The best combination of probes for *Heterosigma akashiwo* and *Fibrocopsa japonica* were then tested for specificity in the S.H.A format. FIG. 1 shows specificity and isolate comparison for the sandwich hybridization assay combinations targeted at *H. akashiwo* and *F. japonica*. A). The probe combination Het1.25aS (SEQ ID NO:15)/Rapid1F (SEQ ID NO:8) which is targeted at *H. akashiwo* was screened against a number of *H. akashiwo* isolates and other raphidophyte species. *H. akashiwo*1 represents the isolate *H. akashiwo* CAWR04; *H. akashiwo* 2=CAWR05; *H. akashiwo* 3=CAWR09 and *H. akashiwo* 4=CAWR14. The *F. japonica* isolate was CAWR02. B). The probe combination Fib1.25aS/Raphid1F which is targetted at *F. japonica* was screened against two *F. japonica* isolates and other raphidophyte species. *F. japonica* 1 represents the isolate CAWR02 and *F. japonica* 2 represents the isolate CAWR03. The *H. akashiwo* isolate was CAWR05.

Example 8
Standard Curve Construction

The standard curves were constructed by spiking cells which were in log phase growth into 1 L of either filtered sea water (FSW) or field sample, then collecting the cells by gentle filtration and lysing as described above. The concentrated stock solutions were then serially diluted with either lysis/hybridization buffer for the FSW sample or field background for the field sample. Four replicates of each dilution were loaded onto the hybridization plates to check for variation of signal from well to well.

Figure 2:
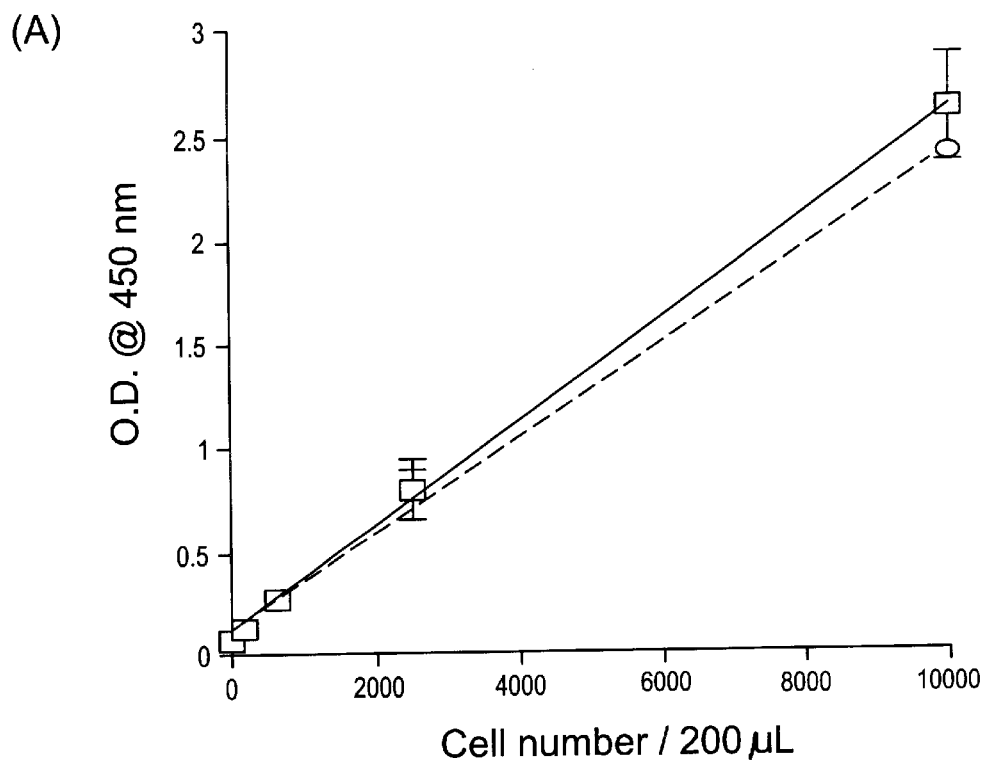
FIG. 2 shows serial dilution standard curves for *F. japonica* and *H. akashiwo* based on the sandwich hybridization assay. In A) a standard curve at 450 nm for *F. japonica* cells spiked into field and filtered sea water background is shown. In B) a standard curve at 450 nim for *H. akashiwo* cells spiked into field and filtered sea water background is shown.
Figure 2:
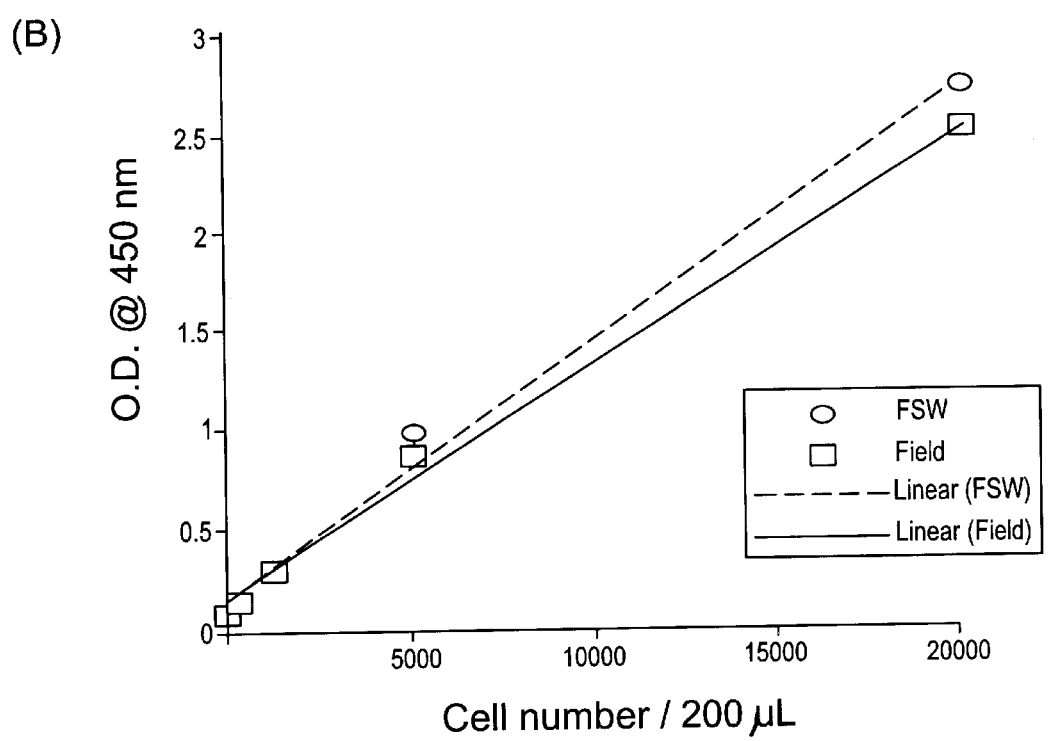

FIG. 2 shows serial dilution standard curves for *F. japonica* and *H. akashiwo* based on the sandwich hybridization assay, A) standard curve at 450 nm for *F. japonica* cells spiked into field and filtered sea water (FSW) background; B) standard curve at 450 nm for *H. akashiwo* cells spiked into field and FSW background.

The differences between the spiked-FSW and field sample standard curves for both *Heterosigma akashiwo* and *Fibrocapsa japonica*, were non-significant, indicating that a complex field background has minimal impact with regard to efficacy and sensitivity of the S.H.A.'s for *Heterosigma akashiwo* and *Fibrocapsa japonica*.

Example 9
Signal Comparison Over a Complete Growth Cycle

The signal generated by cells though a growth cycle was examined by innoculating two batch culture per species (1 L of f/2 media in 5 L flasks) with 1000 *Heterosigma akashiwo* cells $mL_{-1}$ and 500 *Fibrocapsa japonica* cells $mL_{-1}$ respectively. These cultures were grown under a 12:12 LD photoperiod at 20±1° C. Samples were collected at regular intervals covering the entire growth cycle. The *Heterosigma akashiwo* samples were preserved with Lugols Iodine, and at least three 10 μL aliquots were counted. *Fibrocapsa japonica* was preserved with the ethanol/saline fixative and counted as for *Heterosigma akashiwo*. Lugols Iodine preserved *Fibrocapsa japonica* resulted in clumped cells which were not quantifiable. The S.H.A. lysates were prepared by collecting 20,000 *Heterosigma akashiwo* cells 1 ml lysate$^{-1}$ and 10,000 *Fibrocapsa japonica* cells 1 ml lysate$^{-1}$, which corresponds to 4000 and 2000 cells well$^{-1}$ (well=0.2 ml) respectively. These samples were stored at −80° C. and once all samples were collected they were screened with the S.H.A. The samples were processed in one lot to minimize any differences in various batches of S.H.A. plates and reagents.

There was no significant difference between the FSW and field treatment standard curves for either *Heterosigma akashiwo* or *Fibrocapsa japonica*. The results for *Heterosigma akashiwo* and *Fibrocapsa japonica* are displayed in FIG. 1.

Preferred long-term storage of lysate is considered to be storage of samples at −80° C. for extended periods of time. A large batch of lysate was prepared, split into aliquots and frozen at −80° C. to check the effect of storage on signal. At various times over a year, a sample was removed and analyzed to check for degradation and subsequent signal deduction and the effect of multiple freeze/thaw cycles was tested although data are not provided here.

Samples which were required for later analyses were stored at −80° C. These samples were immediately stored either as a lysate or as cells filtered down onto a membrane. The lysates showed no appreciable drop in signal over an entire year of storage, whereas the processing of cells which had been filtered onto membranes resulted in a substantial decrease in signal. Repeated freeze/thaw cycles of the lysate also resulted in the rapid decrease of signal.

The growth cycle experiment showed a 2-fold signal variation for *Heterosigma akashiwo* between the two batches in the first 9 days of the culture, but after day 9 the signal from the batches was comparable. In late stationary phase where the cultures were starting to die, there was a 2-fold decrease in signal. For *Fibrocapsa japonica* there was a variance of about 2-fold over the entire growth cycle with no appreciable dropoff in signal at late stationary phase growth. The results for *Heterosigma akashiwo* and for *Fibrocapsa japonica* are displayed in FIG. 2.

Figure 3:
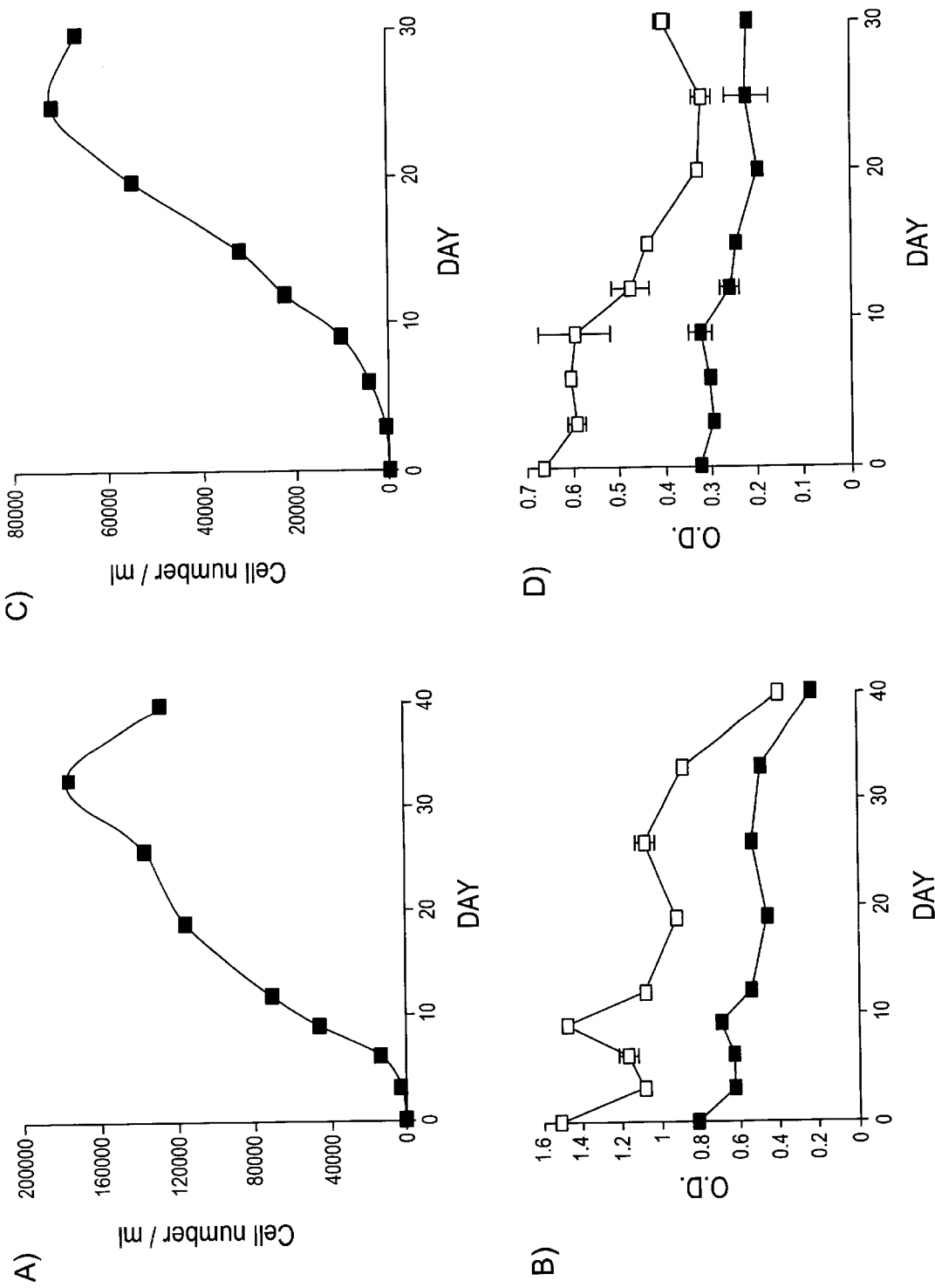
FIG. 3 shows ribosomal RNA levels as measured using the sandwich hybridization assay over an entire growth cycle for *H. akashiwo* and *F. japonica*. In the graphs B and D the open box data points represent signal at 450 nm, whereas the closed circles represent signal at 655 nm. In A) changes in cell density over a growth cycle for a batch culture of *H. akashiwo* is shown. In B) signal from the sandwich hybridization assay for a constant number of cells over a growth cycle of *H. akashiwo* is shown. In C) changes in cell density over a growth cycle for a batch culture of *F. japonica* is shown. In D) signal from the sandwich hybridization assay for a constant number of cells over a growth cycle of *F. japonica* is shown.

FIG. 3 shows ribosomal RNA levels as measured using the sandwich hybridization assay over an entire growth cycle for *H. akashiwo* and *F. japonica*. In the graphs B and D the open box data points represent signal at 450 nm, whereas the closed circles represent signal at 655 nm; A) Changes in cell density over a growth cycle for a batch culture of *H. akashiwo*; B) Signal from the sandwich hybridization assay for a constant number of cells over a growth cycle of *H. akashiwo*; C) Changes in cell density over a growth cycle for a batch culture of *F. japonica*; D) Signal from the sandwich hybridization assay for a constant number of cells over a growth cycle of *F. japonica*.

The determinations of signal from cells grown over an entire growth cycle using batch cultures showed that the signal only varied by a factor of 2, except for dying cells in late stationary phase growth for *Heterosigma akashiwo*. Using F.I.S.H. analyses there is an order of magnitude decrease in signal for cells entering late stationary phase growth. The difference in observations for F.I.S.H. and S.H.A. formats suggests that the rRNA in preserved cells may not be as accessible due to the increase in polysaccharides in cells and/or the protein interaction with rRNA. Further research into these observations is required to gain insight into the fate of rRNA pool during a growth cycle. Further, these observations are based on cultured lysates and may not reflect the situation in the field. The variation between signal in the *Heterosigma akashiwo* batch cultures is evident in the first 9 days of growth. These differences may be due to inaccurate counts and it was also observed that one of the cultures had significant aggregation/sticking of cells to side of flask during these 9 days.

No non-specific signal production for either combination of probes has been observed for cultured species or field samples. The probe combinations for *Heterosigma akashiwo* and *Fibrocapsa japonica* gave a signal from the S.H.A. which was comparable for all geographic isolates of the target species.

Example 11

Field Trials

The preliminary field trials using the S.H.A have detected *Fibrocapsa japonica* in low numbers (2–3000 cells $L^{-1}$, which corresponds to 160 and 240 cells $well^{-1}$ respectively) at three locations in the Hauraki Gulf, East Coast of the North Island, New Zealand. These results were confirmed independently by the commercial monitoring team of the Cawthron Institute, Nelson, New Zealand, using traditional methodology. One unconfirmed 'positive' result has been registered for *Heterosigma akashiwo* in a sample collected from the Santa Cruz pier, Santa Cruz, Calif.

Field trials were conducted on sandwich hybridization assays for *Heterosigma akashiwo* and *Fibrocapsa japonica* using opportunistic samples sent to the Cawthron Institute commercial monitoring team, Nelson, New Zealand. The sandwich hybridization assay for *Heterosigma akashiwo* and *Fibrocapsa japonica* was compared against standard light microscopy counts. Their counts were based on a single 10 mL sub-sample of the acid Lugol's Iodine preserved samples. Overall, comparisons of cell numbers as counted by light microscopy and the S.H.A. are in good agreement. No false positives were observed and all samples that contained either *Heterosigma akashiwo* or *Fibrocapsa japonica* above the lower limit of detection were detected using the S.H.A. This observation indicates that New Zealand populations of these two species have minimal genetic diversity at the Large Subunit rRNA (LSU rRNA) gene level. Also, work on cultured isolates from Australia, Canada, Europe, Japan, Korea, and the USA indicate that global populations of *Heterosigma akashiwo* and *Fibrocapsa japonica* are relatively homologous based on the LSU rRNA gene. This result is extremely beneficial for the deployment of this assay for these species globally. In a recent paper submitted for the proceedings of the 9th International Conference on Harmful Algal Blooms Conference, Tasmania, Australia, Rhodes et al. Concluded ". . . it is clear that this assay is now ready to be integrated into a suite of monitoring tools for both fish far managers . . . ".

We claim:

1. An isolated oligonucleotide consisting of the nucleotide sequence of SEQ ID NO: 15.

2. An oligonucleotide kit for detection of raphidophyte cells comprising an oligonucleotide consisting of the nucleotide sequence of SEQ ID NO: 15.

3. The kit of claim 2 further including one or more hybridization buffers.

* * * * *